(12) United States Patent
Gurev et al.

(10) Patent No.: US 11,687,691 B2
(45) Date of Patent: Jun. 27, 2023

(54) FORWARD AND REVERSE TRANSFORMATIONS OF A MODEL OF FUNCTIONAL UNITS OF A BIOLOGICAL SYSTEM TRAINED BY A GLOBAL MODEL OF THE SYSTEMS

(71) Applicant: International Business Machines Corporation, Armonk, NY (US)

(72) Inventors: Viatcheslav Gurev, Bedford Hills, NY (US); Paolo Di Achille, Pleasantville, NY (US); Jaimit Parikh, Danbury, CT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1212 days.

(21) Appl. No.: 16/239,139

(22) Filed: Jan. 3, 2019

(65) Prior Publication Data
US 2020/0218786 A1 Jul. 9, 2020

(51) Int. Cl.
*G06F 30/23* (2020.01)
*G06N 20/00* (2019.01)
(Continued)

(52) U.S. Cl.
CPC ............. *G06F 30/23* (2020.01); *G06N 3/008* (2013.01); *G06N 5/025* (2013.01); *G06N 20/00* (2019.01);
(Continued)

(58) Field of Classification Search
None
See application file for complete search history.

(56) References Cited

U.S. PATENT DOCUMENTS 7,828,735 B2 11/2010 Holmes et al.
8,527,251 B2 9/2013 Ionasec et al.
(Continued)

FOREIGN PATENT DOCUMENTS

JP 2016515843 A 6/2016
WO 2015073927 A2 5/2015

OTHER PUBLICATIONS

Moosavi et al., "Efficient construction of local parametric reduced order models using machine learning techniques," arXiv preprint arXiv: 1511.02909 (2015) (Year: 2015).*

(Continued)

*Primary Examiner* — Anh-Tuan V Nguyen
(74) *Attorney, Agent, or Firm* — Amin, Turocy & Watson, LLP

(57) ABSTRACT

Systems, computer-implemented methods, and computer program products that can facilitate a transformation of a model of an entity by a model of a plurality of entities are provided. According to an embodiment, a computer-implemented method can comprise identifying a plurality of parameters of a model of a plurality of entities; generating a model of an entity based on collected data of an operation of the entity, wherein the model of the entity comprises a subset of the plurality of parameters; and transforming the model of the entity based the model of the plurality of entities such that a first result from the model of the plurality of entities and a second result from the model of the entity have a relationship that satisfies a defined criterion, given same values used for the subset of the plurality of parameters.

20 Claims, 22 Drawing Sheets

(51) Int. Cl.
| | |
|---|---|
| *G16H 30/20* | (2018.01) |
| *G06T 7/00* | (2017.01) |
| *G06N 3/008* | (2023.01) |
| *G06N 5/025* | (2023.01) |
| *G06F 111/10* | (2020.01) |
| *G06F 111/20* | (2020.01) |

(52) U.S. Cl.
CPC ........... *G06T 7/0014* (2013.01); *G16H 30/20* (2018.01); *G06F 2111/10* (2020.01); *G06F 2111/20* (2020.01); *G06T 2207/20081* (2013.01); *G06T 2207/30048* (2013.01)

(56) References Cited

U.S. PATENT DOCUMENTS

| | | | |
|---|---|---|---|
| 2007/0014457 A1* | 1/2007 | Jolly | G06T 7/12 382/128 |
| 2010/0070249 A1 | 3/2010 | Ionasec et al. | |
| 2012/0226482 A1* | 9/2012 | Wu | G06F 30/23 703/2 |
| 2013/0304683 A1* | 11/2013 | Lo | G06N 3/049 706/20 |
| 2013/0323761 A1 | 12/2013 | Sheikh et al. | |
| 2015/0242589 A1 | 8/2015 | Neumann et al. | |
| 2015/0347709 A1* | 12/2015 | Mansi | G16H 50/50 703/11 |
| 2016/0210435 A1 | 7/2016 | Neumann et al. | |
| 2019/0133537 A1* | 5/2019 | Ghose | A61B 5/725 |
| 2020/0302096 A1* | 9/2020 | Münz | G06F 30/20 |
| 2022/0059229 A1* | 2/2022 | Chen | G16Z 99/00 |

OTHER PUBLICATIONS

Niederer, Steven, A., et al. "Computational models in cardiology" Nature Reviews, Cardiology, Oct. 25, 2018. 12 pages.
Di Achille, Paolo, et al. "Gaussian Process Regressions for Inverse Problems and Parameter Searches in Models of Ventricular Mechanics." Frontiers in Physiology, Aug. 14, 2018. 17 pages.
Moulton, Michael, J., et al. "Simulation of Left Ventricular Dynamics Using a Low-Order Mathematical Model." Cardiovascular Engineering and Technology, vol. 8, No. 4, Dec. 2017, pp. 480-494. 15 pages.
Gurev, Viatcheslav, et al. "A high-resolution computational model of the deforming human heart." Biomech Model Mechanobiol. 2014. 21 pages.
Hayenga, Heather NO., et al. "Ensuring Congruency in Multiscale Modeling: Towards Linking Agent Based and Continuum Biomechanical Models of Arterial Adaptation." Annals of Biomedical Engineering, vol. 39, No. 11, Nov. 2011. 14 pages.
Sugiura, Seiryo, et al. "Multi-Scale Simulations of Cardiac Electrophysiology and Mechanics Using the University of Tokyo Heart Simulator." Progress in Biophysics and Molecular Biology 110 (2012) 380-389. 10 pages.
Gima, Kazutaka, et al. "Ionic Current Basis of Electrocardiographic Waveforms A Model Study." Circ Res. May 3, 2002; 90(8): 889-896. 16 pages.
Land, Sander, et al. "A model of cardiac contraction based on novel measurements of tension development in human cardiomyocytes." Journal of Molecular and Cellular Cardiology, 106, 68-83. doi: 10.1016/j.yjmcc.2017.03.008. 28 pages.

Rozza, G., et al. "Reduced Basis Approximation and a Posteriori Error Estimation for Affinely Parametrized Elliptic Coercive Partial Differential Equations." Arch Comput Methods Eng (2008) 15: 229-275. 47 pages.
Marsden, Alison L.. "A computational framework for derivative-free optimization of cardiovascular geometries." Comput Methods Appl. Mech. Engrg. 197 (2008) 1890-1905. 17 pages.
Marsden, Alison L.. "Optimization in cardiovascular modeling." Annu. Rev. Fluid Mech. 2014. 46:519-46. 29 pages.
Rice, John Jeremy, et al. "Approximate Model of Cooperative Activation and Crossbridge Cycling in Cardiac Muscle Using Ordinary Differential Equations." Biophysical Journal. Sep. 2008;95(5): 2368-90. 23 pages.
Razumova, Maria, et al. Stiffness-distortion sarcomere model for muscle simulation. Journal of Applied Physiology. 1999;87(5): 1861-1876. 16 pages.
Saltelli, Andrea, et al. "Settings and methods for global sensitivity analysis—a short guide." PAMM • Proc. Appl. Math. Mech. 7, 2140013-2140014 (2007). 2 pages.
Kucherenko, Sergei, et al. "Sobol' Indices for Problems Defined in Non-Rectangular Domains." Reliability Engineering and System Safety. 2017. 24 pages.
Berkooz, Gal, et al. "The proper orthogonal decomposition in the analysis of turbulent flows." Annual Review of Fluid Mechanics 1993;25(1): 539-75. 37 pages.
Usyk, T.P., et al. "Effect of Laminar Orthotropic Myofiber Architecture on Regional Stress and Strain in the Canine Left Ventricle." Journal of Elasticity 61: 143-164, 2000. 22 paes.
Young, Robert J., et al. "Anisotropy of wave propagation in the heart can be modeled by a Riemannian electrophysiological metric." PNAS, Aug. 24, 2010, vol. 107, No. 34. 6 pages.
Radau, P., et al. "Evaluation Framework for Algorithms Segmenting Short Axis Cardiac MRI." the MIDAS Journal, 2009. 7 pages.
Baillargeon, Brian, et al. "The Living Heart Project: A robust and integrative simulator for human heart function." European Journal of Mechanics / A Solids (2014), doi: 10.1016/j.euromechsol.2014. 04.001. 13 pages.
Lamata, Pablo, et al. "Images as Drivers of Progress in Cardiac Computational Modelling." Progress in Biophysics and Molecular Biology (2015). 15 pages.
Xi, Jiahe, et al. "The estimation of patient-specific cardiac diastolic functions from clinical measurements." Medical Image Analysis 17 (2013) 133-146. 14 pages.
Pagani, Stefano. "Reduced-order Models For Inverse Problems And Uncertainty Quantification In Cardiac Electrophysiology," Doctoral Dissertation, Politecnico Di Milano Mox—Dipartimento Di Matematica Modelli E Metodi Matematici Per L'ingegneria, Italy, 2017.. 210 pages.
Nasopoulou, Anastasia, et al. "Improved identifiability of myocardial material parameters by an energy-based cost function." Biomech Model Mechanobiol (2017) 16:971-988. 18 pages.
Chabiniok, Radomir, et al. "Multiphysics and multiscale modelling, data-model fusion and integration of organ physiology in the clinic: ventricular cardiac mechanics." The Royal Society Publishing, Feb. 19, 2016. DOI: 10.1098/rsfs.2015.0083. 24 pages.
Stergiopulos, Nikos, et al. "Determinants of stroke vol. and systolic and diastolic aortic pressure." Am. J. Physiol. Heart Circul. Physiol. 270, H2050-H2059. doi: 10.1152/ajpheart.1996 270.6. H2050. 10 pages.
Lumens, Joost, et al. "Three-Wall Segment (TriSeg) Model Describing Mechanics and Hemodynamics of Ventricular Interaction." Annals of Biomedical Engineering, vol. 37, No. 11, Nov. 2009 pp. 2234-2255. 22 pages.

* cited by examiner

US 11,687,691 B2

FORWARD AND REVERSE TRANSFORMATIONS OF A MODEL OF FUNCTIONAL UNITS OF A BIOLOGICAL SYSTEM TRAINED BY A GLOBAL MODEL OF THE SYSTEMS

The subject disclosure relates to models of biological systems, and more specifically, to transforming models of biological systems.

SUMMARY

The following presents a summary to provide a basic understanding of one or more embodiments of the invention. This summary is not intended to identify key or critical elements, or delineate any scope of the particular embodiments or any scope of the claims. Its sole purpose is to present concepts in a simplified form as a prelude to the more detailed description that is presented later. In one or more embodiments described herein, systems, computer-implemented methods, and/or computer program products that facilitate a transformation of a model of an entity by a model of a plurality of entities.

According to an embodiment, a system can comprise a memory that can store computer executable components and a processor that can execute the computer executable components stored in the memory. The computer executable components can include a parameter identifying component that can identify a plurality of parameters of a model of a plurality of entities and a model generator that can generate a model of an entity based on collected data of an operation of the entity, the model of the entity comprising a subset of the plurality of parameters. The computer executable components can further include a model transformer that can transform the model of the entity based on information from the model of the plurality of entities corresponding to the subset of the plurality of parameters. The transforming the model of the entity can result in a first result from the model of the plurality of entities and a second result from the model of the entity having a relationship that satisfies a defined criterion, given same values used for the subset of the plurality of parameters.

According to another embodiment, a computer-implemented method can comprise identifying, by a system operatively coupled to a processor, a plurality of parameters of a model of a plurality of entities and generating, by the system, a model of an entity based on collected data of an operation of the entity, the model of the entity comprising a subset of the plurality of parameters. The model of the entity can be transformed based on information from the model of the plurality of entities corresponding to the subset of the plurality of parameters. The transforming the model of the entity can result in a first result from the model of the plurality of entities and a second result from the model of the entity having a relationship that satisfies a defined criterion, given same values used for the subset of the plurality of parameters.

According to another embodiment, a computer program product facilitating a transformation of a model of an entity by a model of a plurality of entities can comprise a computer readable storage medium having program instructions embodied therewith. The program instructions are executable by a processor to cause the processor to identify a plurality of parameters of a model of a plurality of entities and generate the model of the entity based on collected data of an operation of the entity, the model of the entity comprising a subset of the plurality of parameters. The program instructions can also cause the processing component to transform the model of the entity based on information from the model of the plurality of entities corresponding to the subset of the plurality of parameters, the transforming of the model of the entity can result in a first result from the model of the plurality of entities and a second result from the model of the entity having a relationship that satisfies a defined criterion, given same values used for the subset of the plurality of parameters.

DETAILED DESCRIPTION

Figure 1:
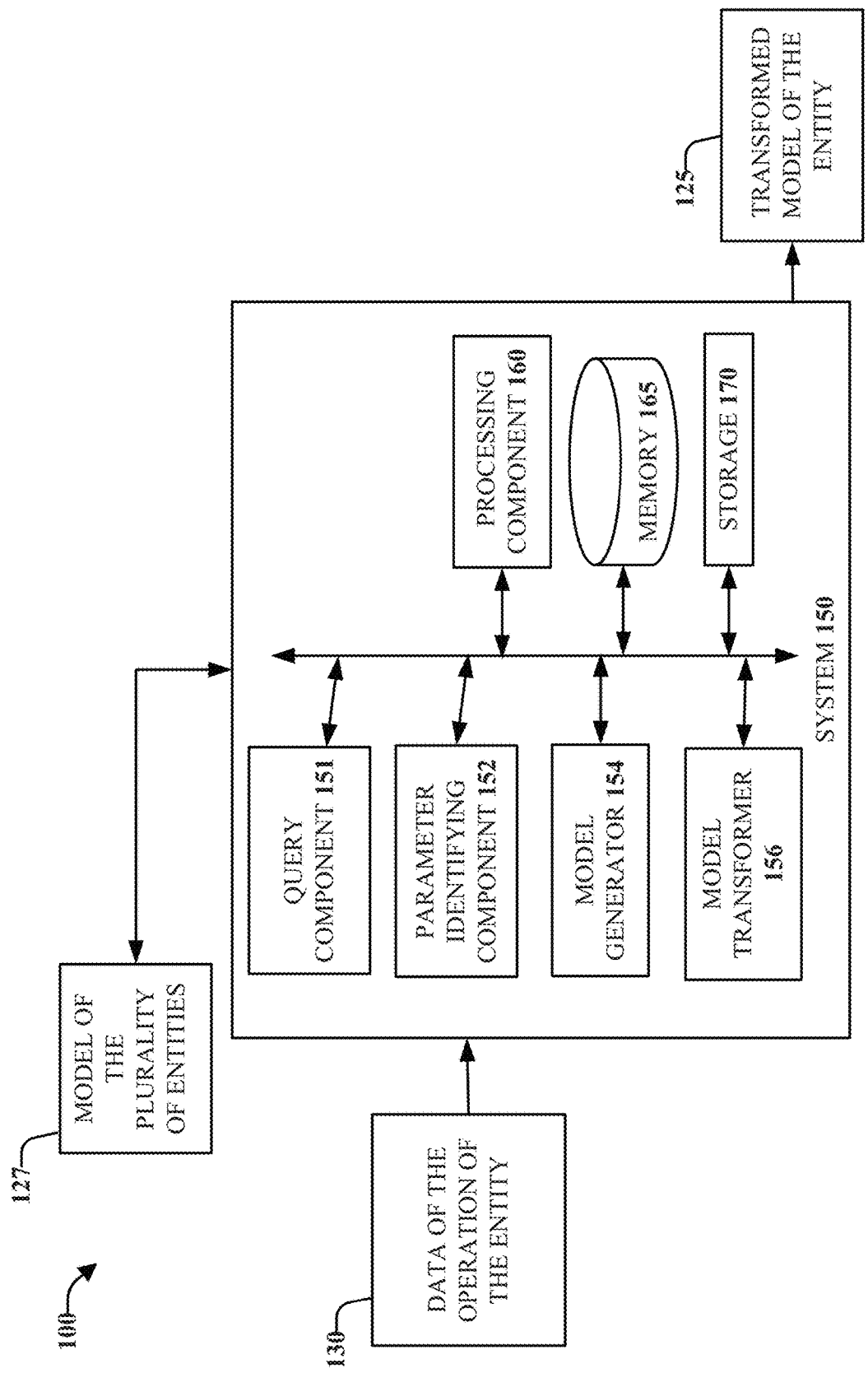
FIGS. 1-3 illustrate block diagrams of different aspects of an example, non-limiting system that can facilitate the transformation of one model using another model in accordance with one or more embodiments described herein.

The following detailed description is merely illustrative and is not intended to limit embodiments and/or application or uses of embodiments. Furthermore, there is no intention to be bound by any expressed or implied information presented in the preceding Background or Summary sections, or in the Detailed Description section.

One or more embodiments are now described with reference to the drawings, wherein like referenced numerals are used to refer to like elements throughout. In the following description, for purposes of explanation, numerous specific details are set forth in order to provide a more thorough understanding of the one or more embodiments. It is evident, however, in various cases, that the one or more embodiments can be practiced without these specific details. It is noted that the drawings of the present application are provided for illustrative purposes only and, as such, the drawings are not drawn to scale.

In one or more embodiments described herein, the behavior of complex systems can result from coupled interactions between large populations of related entities that share similar properties and act in coordination. For example, the behavior of many complex biological systems can be effectively interpreted as resulting from coupled interactions between large populations of related entities (e.g., cardiac cells) that share similar properties and act in coordination (e.g., in response to cardiac pacing stimuli). It is important to note that the embodiments described herein that can operate in a biological context are not limiting, and that other types of entities can be used with one or more embodiments described herein.

For convenience, as used herein, a model of related entities (e.g., cells) can also be represented by a transformed model of an entity. This transformed model of an entity created and/or used by one or more embodiments is termed a "low-order model." In one or more examples described herein, the functional unit (e.g., the entity) that is the subject of the models discussed above is a part of biological system of a biological unit, e.g., the part of biological system corresponding to populations of cardiac muscle cells as a part of the human cardiovascular system.

Also for convenience, models of a plurality of entities described herein can be termed a "multiscale model" or a "global model," with a Finite Element (FE) model being an implementation of these types of models. Global models can be composed of multiple elements, and these elements can incorporate models of biological units (e.g., similar to modeling of cardiac muscle cells), and/or other biological systems. Example models of biological systems include phenomenological time-varying elastance model based on simplistic assumptions on ventricular geometry, and a structural 3-D FE model, which can capture in detail, anatomy and material properties of ventricular mechanics. It is important to note that these terms used for convenience are not limiting, and other types of models can be used in one or more embodiments described herein.

One or more embodiments can create/and or use a model of an entity that can be transformed based on information from a model of a plurality of entities (e.g., populations of cells) to a low-order model that can describe the operation of the plurality of entities (e.g., an organ, a heart) with results that can be comparable to the FE model, but with reduced processing time and complexity. Examples of such transformations in one or more embodiments include the creation and transformation of low-order myocyte to heart models, which can simulate cardiac pumping function transforming the simulated contraction of a cardiac cell, or compute an electrocardiogram (ECG) transforming the simulated action potential of a cardiac cell.

FIG. 1 illustrates a block diagram of an example, non-limiting system 150 facilitating a transformation, based on information from a model of a plurality of entities (FE model), of a model of an entity to a low-order model that can describe the operation of a plurality of entities. System 150 can receive collected data of an operation of the entity 130, and system 150 can include a parameter identifying component 152, a model generator 154, and a model transformer 156 in accordance with one or more embodiments described herein. As described with FIGS. 2 and 3 below, query component 151 can query models with sets of parameters used as input and return results based on the model. Repetitive description of like elements employed in other embodiments described herein is omitted for sake of brevity.

To facilitate processes, store results, and provide storage for processor executable components, system 150 can access memory 165 and storage 170, and these can respectively be, for example, a Random Access Memory (RAM) and a hard drive. Processing component 160 can receive executable instructions from memory 165 and storage 170, and can execute functional components, such as 151, 152, 154, and 156 discussed herein.

Figure 3:
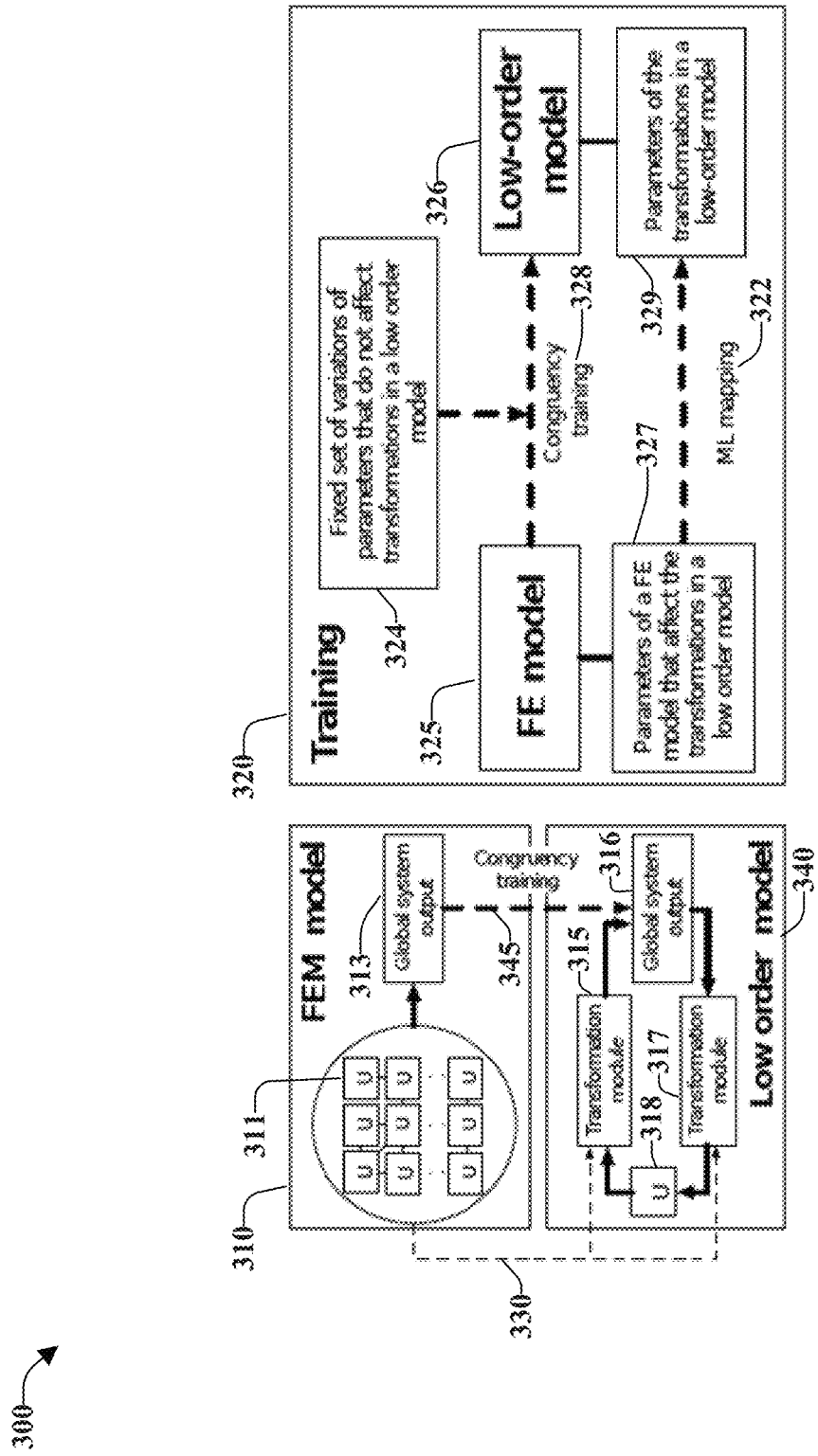

In one or more embodiments that can use the components of FIG. 1, parameter identifying component 152 can analyze the model of the plurality of entities 127 to identify a plurality of parameters that can be used to transform the model of the entity (this analysis and identification of parameters is discussed in greater detail with FIG. 3). The generation of this model of the entity and of the related transformation can be based on collected data of an operation of the entity 130. Using the identified plurality of parameters, model generator 154 can select a subset of the identified parameters that can be used by the model of the entity transformed to a low-order model.

As discussed further with FIG. 3 below, model transformer 156, in one or more embodiments, can transform the model of the entity based on information from the model of the plurality of entities 127, and this information can correspond to the selected subset of the plurality of parameters. This transforming can result in a transformed model of the entity 125. Using transformed model of the entity 125 by one or more embodiments can yield in results that are substantially similar to results of using model of the plurality of entities 127. As discussed further below, because in one or more embodiments transformed model of the entity 125 can require less processing than the model of the plurality of entities 127 to output results, the transformation performed by some embodiments can yield improvements compared to obtaining results using the model of the plurality of entities 127.

In an example, in one or more embodiments, two linear transformations can be used to construct a low-order model, e.g., a low-order model of a cardiac pumping function. In this example, a transformation can be a linear transformation between active tension of the sarcomere (contractile unit of the myocyte) and the pressure generated by the 3-D finite element model of a ventricle, e.g., establishing a relationship between the results of a model comprising a population of cells (e.g., cardiomyocytes) and a low-order model of cardiac mechanics Another example of a transformation that can be used by one or more embodiments is a linear transformation between strain of the sarcomere and a geometric feature of the 3-D finite element model of a ventricle (e.g., the intraventricular volume). In these examples, coupling of sarcomere mechanics and organ mechanics can be attained by one or more embodiments through empirical transformations that, despite not having an obvious biophysical meaning, can reproduce with great accuracy the global results of a more complex multiscale FE model of ventricular mechanics, e.g., the transformed model can capture the role of both anatomy and architectural organization of myocardium. One or more embodiments that can determine and utilize relationships between cell mechanics and cardiac mechanics are discussed in more detail with FIGS. 4 and 5 below.

System 150 and similar embodiments described herein can employ hardware and/or software to solve problems that are highly technical in nature (including for example generating, analyzing, transforming and using models of entities), that are not abstract and that cannot be performed as a set of mental acts by a human. Further, in certain embodiments, some of the processes performed can be performed by one or more specialized computers (e.g., one or more specialized processing units, a specialized computer such as a computer specialized for tomography and reconstruction, statistical estimation, and so on) for carrying out defined tasks related to machine learning. System 150 and/or components of system 150 can be employed to solve new problems that arise through advancements in technologies mentioned above, computer architecture, and/or the like.

Figure 2:
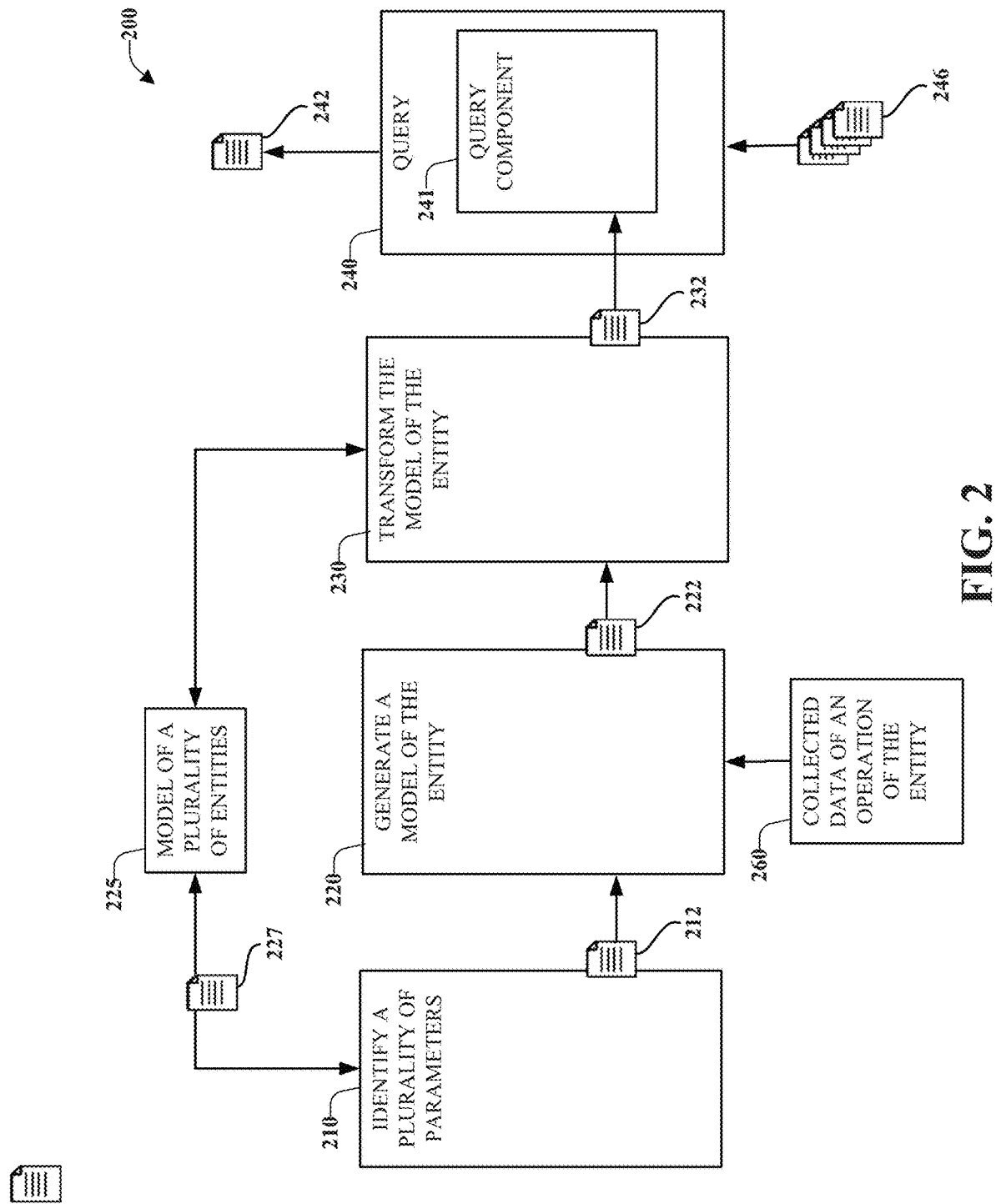

FIG. 2 illustrates a block diagram 200 that represents a more detailed description of processes similar to those used by embodiments discussed above. Repetitive description of like elements and/or processes employed in respective embodiments is omitted for sake of brevity.

In block 210 a plurality of parameters 227 can be identified in a model of a plurality of entities 225. In block 220, a model of the entity can be generated based on inputs that can include the identified plurality of parameters 212 and collected data of an operation of the entity 260. In block 230, the model of the entity can be transformed based on inputs that can include an identified subset of the plurality of parameters 222 and information from the model of the plurality of entities 225. In block 240, query component 241 can receive the transformed model of the entity (i.e., the low-order model) 232 and parameter inputs 246, and provide results 242.

In one or more embodiments, low-order models can be based on two classes of parameters. Unlike standard biophysical models, the first class of "trained" parameters can have no direct links to the underlying biophysics of the subject of the low-order model (e.g., models of cardiac mechanics or models of an organ), rather, these parameters can modulate a machine learning model used by one or more embodiments to match the outputs of detailed biophysical models, for example, FE models discussed above (e.g., model of a plurality of entities 225). The second class of "physical" parameters can maintain a biophysical meaning, and this feature can provide more flexibility than pure machine learning approaches. One or more embodiments can identify trained parameters by identifying parameters that modulate the transformation of the outputs of single units (e.g., cell models) to the global outputs of the FE model (e.g., organ model).

As described above with FIG. 1, a transformation (as in block 230) that can be used by one or more embodiments can be a linear operator (e.g., a scaling matrix or linear regression) defined by an identified set of trained parameters. Based on the identification of the parameters of the linear operator to be trained, training can then then be performed by ensuring congruency between outputs of the low-order model and of FE models upon a set of perturbed conditions, this process also being termed herein "congruency training," described in more detail with FIG. 3 below.

FIG. 3 illustrates a more detailed block diagram of an example, non-limiting system that depicts an example model of a plurality of entities (FE model (FEM) 310) that can be used to transform an example model of an entity, e.g., low-order model 340. It should be noted that, as used herein, "transforming" a model of an entity to a low-order model can also be described as "training" a low-order model, e.g., using the structure and/or values of one model to change the structure and/or values of another model. For example, FIG. 3 provides additional detail regarding the transformation of a model of an entity based on information from the FE model 310 in a box on FIG. 3 labeled training 320. It should be noted that these characterizations of operations performed by one or more embodiments should not be interpreted as limiting. Repetitive description of like elements and/or processes employed in respective embodiments is omitted for sake of brevity.

As noted above, a typical FE model can be composed of multiple elements (e.g., models of biological units for example), these elements being incorporated as a number of finite elements 311. Coupled interactions between FEs and the imposed boundary conditions ultimately result in the global outputs of the FE model.

In one or more embodiments, features of an FE model can be selected (e.g., a subset of parameters of the FE model) and mapped 330 to parameters (e.g., a corresponding subset of parameters) of transformation modules 315 and 317 of low-order model 340. This selecting and mapping can be performed, for example, using machine learning techniques described herein. One approach to transforming the unit model 318 based on the selected subset of parameters can use a set of simulated scenarios where models run are repeated for perturbed physical parameters that can be provided by the selecting and mapping process 330 described above.

To provide matching (e.g., similarity) conditions for the transformation cycles noted above in one or more embodiments, finite elements 311 and global system output 313 of FE model 310 can be compared to global system output 316 of low-order model 340 during congruency training 345. With this comparison, similarity conditions can be established to tune parameters of the transformation modules 315 and 317, e.g., low-order model can be trained based on information from one or more of finite elements 311 of FE model 310. One or more embodiments can use these similarity conditions to promote congruency between the FE model and the low-order model, e.g., congruency training can be used herein to describe this process.

In one or more embodiments described herein, transformation of the model of the entity can yield results from the model (e.g., by query component 151) of the plurality of entities and results from the model of the entity that have a relationship that satisfies a defined criterion, given same values used for the subset of the plurality of parameters used for the models as input (e.g., input provided and output received by query component 151). In one or more embodiments, this defined criterion can be a level of similarity, but this example is non-limiting, and other combinations of one or more criteria can be used to compare the result of the models.

For example, in one or more embodiments, parameters selected to transform a model of the entity can be optimized for the low-order model to match pressure-volume behavior of 3-D FEM simulations. Gaussian-Process regression (e.g., Kriging) or other machine learning technique can map changes in some geometric features of a 3-D FE model to variations in low-order model parameters that can modulate the transformations of outputs from the model of the entity to global outputs.

Figure 4:
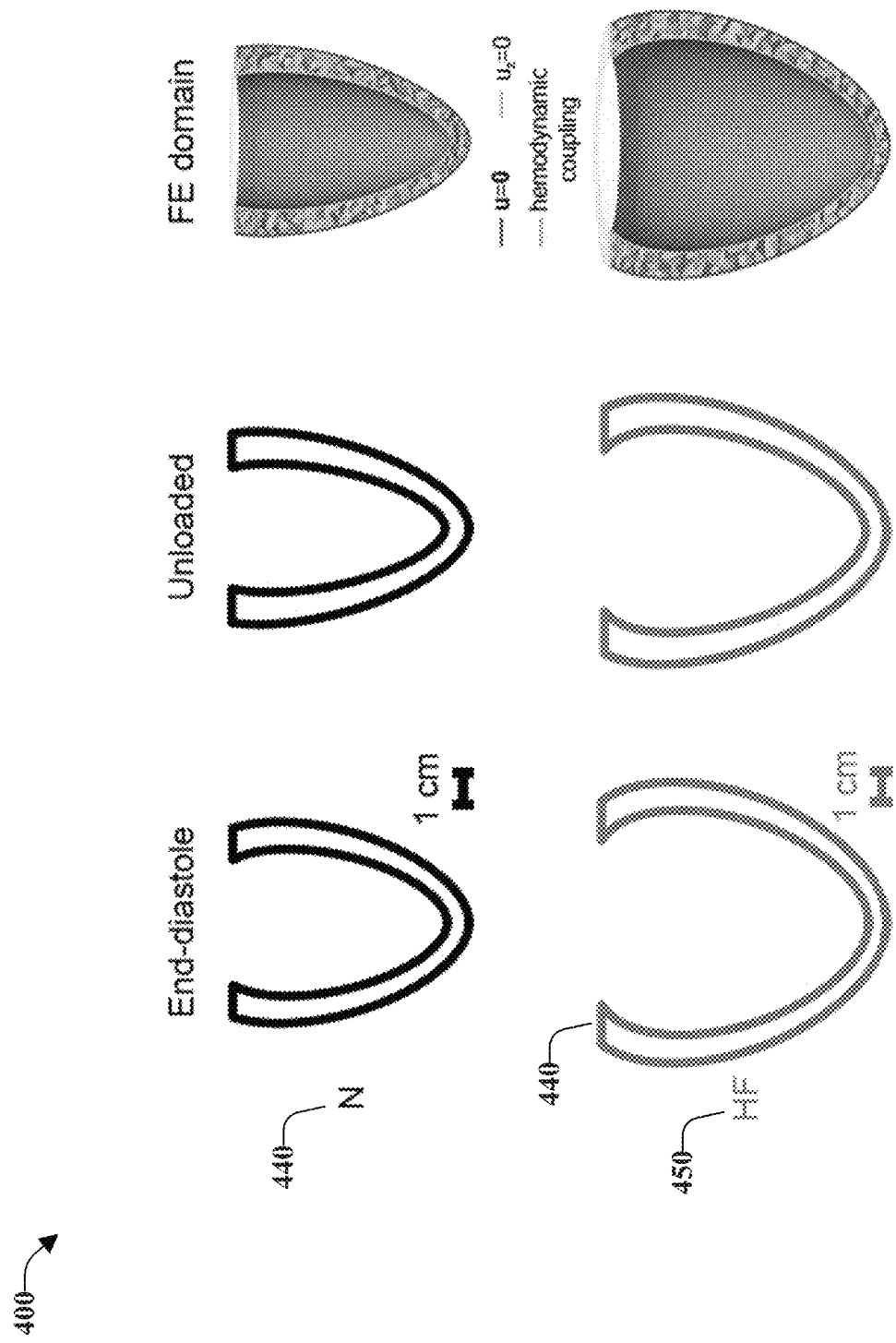
FIG. 4 illustrates an example of a three-dimensional (3-D) model of ventricular mechanics in accordance with one or more embodiments described herein.

FIG. 4 illustrates an example of a plurality of cellular-level models coupled together to describe the macroscopic organ scale in accordance with one or more embodiments described herein. Repetitive description of like elements and/or processes employed in respective embodiments is omitted for sake of brevity.

The example depicted illustrates sample heart geometries that can be used to facilitate the integration of cellular contraction models of myocardial myocytes into a 3-D FE model of soft tissue biomechanics. The example FE model can predict global outputs such as time-varying ventricular volume and pressure, while also naturally accounting for the detailed anatomies of the heart and for the complex boundary conditions acting on it (e.g., to simulate the behavior of the downstream vasculature).

Returning to FIG. 4, this figure illustrates two example left-ventricular geometries that can be used, by one or more embodiments, as representative of normal (N) 440 and heart failure (HF) 450 subject groups that can be extracted, by one or more embodiments, for example, from a cardiac MRI database.

To model the behavior of a left ventricle by processes similar to those discussed herein, one or more embodiments can use geometric representations of ventricular anatomy. One or more embodiments can partially correct for the fact that all imaged ventricle configurations can be subjected to non-negligible loads (e.g., due to intraventricular pressure and external boundary conditions), and the reconstructed geometries can be unloaded by solving an inverse problem.

As an example, geometric descriptions of ventricular geometries at end-diastole and after virtual unloading are shown in Table #1 below:

TABLE #1

| Group | configuration | $R_b$ (mm) | L (mm) | Z (mm) | H (mm) | e | $\Psi_0$ (deg) |
|---|---|---|---|---|---|---|---|
| N | end-diastole | 30 | 8.1 | 43 | 6.9 | 0.7 | −61 |
|   | unloaded | 28 | 9.3 | 45 | 7.6 | 0.65 | −53 |
| HF | end-diastole | 42 | 8.4 | 49 | 5.9 | 0.71 | −73 |
|   | unloaded | 39 | 9.3 | 49 | 6.9 | 0.66 | −73 |

Figure 5:
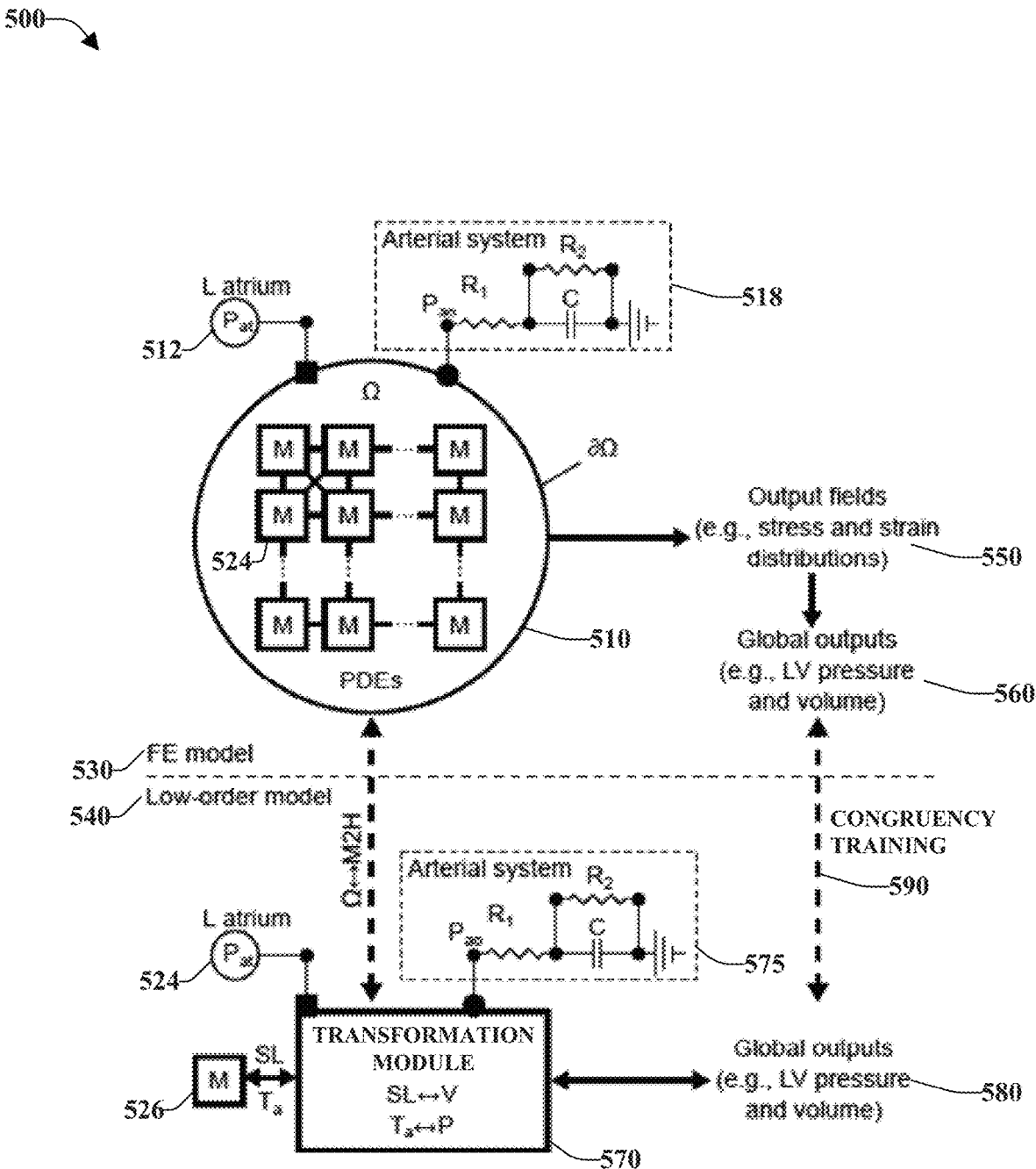
FIG. 5 illustrates a block diagram of two related models having different components in accordance with one or more embodiments described herein.

FIG. 5 illustrates a block diagram that compares schematics of an FE model of ventricular mechanics and a low-order model of ventricular mechanics in accordance with one or more embodiments described herein. Repetitive description of like elements and/or processes employed in respective embodiments is omitted for sake of brevity.

In the examples shown in FIG. 5, schematics of a high-resolution FE model 530 and a corresponding low-order model 540 are shown. As shown, FE model 530 can rely on partial differential equations (PDE) 524 based description of mechanical equilibrium 510 coupled via hemodynamic boundary conditions to a simplified representation of atrial pressure ($P_a$) 512 and to a Windkessel (RCR) model 518 of the downstream vasculature.

As depicted, the example low-order model 540 that can be trained by one or more embodiments can also maintain similar hemodynamic components, e.g., atrial pressure ($P_a$) 524 and Windkessel (RCR) model 575. However, in addition, one or more embodiments can, for example, use transformation module 570 to simplify a description of the computational domain ($\Omega$) to a set of empirical algebraic relationships linking cellular active tension ($T_a$) to ventricular pressure (P), and cellular elongation (SL) to ventricular volume (V). In one or more embodiments, myocytes that act in a highly coordinated manner can have their global behavior reproduced by modeling and transforming at least one equivalent myocyte model (M) 526. This approach, that can use a small number of cells, contrasts in complexity to the use of multiple nonlinear PDEs 524 (e.g., models of multiple coupled cells) that can be required by FE model 530 to yield similar results.

As depicted in FIG. 5, output fields 550, generated by FE model 530 can be used in conjunction to global outputs 580 of transformation module 570 for congruency training 590 of low-order model 540. In one or more embodiments, global outputs 580 can receive parameter values from global outputs 560, and use these mapped parameters for training low-order model 540.

The following example describes how one or more embodiments can use an FE model of the passive mechanical behavior of ventricles to train low-order model 540. For example, in an embodiment, the FE model can be implemented according to a stabilized mixed u-P formulation with ad hoc preconditioning and adapted for P1/P1 elements. In this example implementation, coupling between cellular and elemental stresses and strains can occur implicitly at the Gauss point level. Passive behavior resulting from the complex architectural organization of myocardial fibers can be modeled by one or more embodiments according, for example, to a Fung-type strain energy function, namely by Equation #1 below, where $E_{ij}$(i,j∈{f,s,n}) are components of the Green-Lagrange strain tensor relative to the spatially-varying directions of the myocardial fibers (f), of the myocardial sheets(s) and of the remaining mutually normal direction (n):

$$W_U = \frac{C}{2}(\exp(Q) - 1),$$

$$Q = b_{ff}E_{ff}^2 + b_{ss}E_{ss}^2 + b_{nn}E_{nn}^2 + b_{fs}(E_{fs}^2 + E_{sf}^2) + b_{fn}(E_{fn}^2 + E_{nf}^2) + b_{ns}^2(E_{ns}^2 + E_{sn}^2),$$

Equation #1

In Equation #1, $b_{ij}$(i,j∈{f,s,n}) are material property coefficients expressed in the local reference systems defined by the myocardial fibers and sheets.

To reproduce a behavior similar to Equation #1 a low-order model of one or more embodiments can use empirical relationships that mimic the combined effects of the non-linear hyperelasticity and ventricular geometry used by FE models. An example Equation #2, that can be used by one or more embodiments, can have separate formulations for responses observed at volumes higher and lower than unloaded volume $V_0$, where α, β, γ are coefficients that can modulate the pressure-volume exponential behavior upon compression, and a, b, c are coefficients of the 2-order polynomial that can describe a ventricle under passive tension:

$$\begin{cases} P_{pass} = \alpha\{1 - \exp[\beta\gamma(V - V_0)]\} & \text{if } V \leq V_0 \\ P_{pass} = a(V - V_0)^2 + b(V - V_0) + c & \text{if } V > V_0 \end{cases}$$

Equation #2

One or more embodiments can use the differential treatment of the behavior under compression or tension described above to improve the congruence of the trained low-order model and an FE model.

Active mechanical behavior of ventricles can be modeled by a low-order model by a coupling between active myocyte response and time-varying ventricular hemodynamics, an example of this coupling driving cell action being summarized by Equation #3 below, where S is a vector containing the time-varying state variables of an ODE model of myofilament contraction that depends on calcium concentration, Ca, and on strain of the myofilament, λ. In this example, state variables and strain can also uniquely determine the active tension generated by the myofilament, $T_a$:

$$\begin{cases} \frac{dS}{dt} = f_1(S, \lambda, Ca, t) & ODE \text{ of myofilament model} \\ T_a = f_2(S, \lambda) & m \text{ active tension} \end{cases} \quad \text{Equation \#3}$$

In one or more embodiments, the relationships in Equation #3 can be transformed to incorporate the role played by the coordinated contraction of the left ventricle. In one or more embodiments, when building a low-order model for a given ventricular anatomy of interest, correct sizing of the transformations can be determined. For example, Equation #4 is an equation that can be used by one or more embodiments to model the relationships linking cellular strain to ventricular volume and pressure, where $\mu_1$ and $\mu_2$ can be scaling coefficients of the active component of the low-order model, and $P_{pass}$ can be similar to the corresponding variable in Equation #2 above:

$$\begin{cases} \lambda = \mu_1\left(\frac{V}{V_0} - 1\right) + 1 \\ P = \mu_2 T_a + P_{pass} \end{cases} \quad \text{Equation \#4}$$

It should be noted that, while Equation #4 is specific to ventricular mechanics, one or more embodiments described herein can be used to build low-order models for other biophysical systems.

The congruency training described with FIG. 3 above, and used by one or more embodiments, is described in further detail below. In one or more embodiments, overall best fit coefficients for the linear transformation shown in Equation #4 above can be determined based on high-resolution FE model runs. To improve congruence between a low-order model and its FE model counterpart over a wide range of myocyte lengths and downstream hemodynamic resistances, as discussed further below, one or more embodiments can use one or more active and passive training simulations encompassing varying hemodynamic conditions.

In an example passive training simulation, to extract the passive coefficients α, β, a, b, and c, low-order model predictions can be fitted to FE model pressure-inflation tests run over an intraventricular pressure range, e.g., 0-4 kPa. In contrast, one or more embodiments can select values for the remaining active coefficient parameters (γ, $\mu_1$, $\mu_2$) using an active simulation that can account for different combinations of atrial pressure and Windkessel parameters. Table #2 summarizes this passive and active simulation example:

TABLE #2

| Simulation | $P_a$ (kPa) | $R_1$ | $R_2$ | C |
|---|---|---|---|---|
| ⓟ | 0-4 | — | — | — |
| ① | 0.33 | 0.015 | 0.20 | 8000 |
| ② | 0.66 | 0.015 | 0.05 | 8000 |
| ③ | 1.50 | 0.015 | 0.20 | 8000 |

With respect to different approaches to congruency training described with FIG. 3 above, generally speaking, for any ventricular geometry defined by {$R_b$, L, Z, H, $\Psi_0$, e}, 8 coefficients {α, β, γ, a, b, c, $\mu_1$, $\mu_2$} can be found that can maximize congruence between global outcomes of an FE model and the low-order model to be trained by the congruency training. In one or more embodiments, for a given a set of geometric parameters {$R_b$, L, Z, H, $\Psi_0$, e} the minimization problem of Equation #5 can be solved by one or more embodiments to improve congruence between the FE model and the low-order model, where the subscripts $_{FE}$ and $_{lo}$ are used to label global variables predicted by the FE and low-order models, respectively, and discrepancies can be computed for each training simulation. Finally, {▢, ①, ②, ③} can be the set of congruency training simulations carried out under the boundary conditions shown above in Table #2:

$$\min_{\{\alpha,\beta,\gamma,a,b,c,\mu_1,\mu_2\}} \sum_{i \in \{\text{▢},\text{①},\text{②},\text{③}\}} \left[\left(\frac{V_{FE}(t) - V_{lo}(t)}{V_{FE}(t)}\right)^2 + \left(\frac{P_{FE}(t) - P_{lo}(t)}{P_{FE}(t)}\right)^2\right]_i \quad \text{Equation \#5}$$

One or more embodiments of the low-order models generated based on descriptions herein can ascertain the relative (and potentially coupled) impact of different input parameters on model output metrics. Low-order models described herein can expose both a cellular submodel (e.g., the effective myocyte unit (M) 526 of FIG. 3 described above) and global outputs (e.g., the targets of the linear transformations discussed with Equation #4 above), and can thereby enable the evaluation of varying input parameters at multiple scales ranging from cellular response (e.g., a simulated F-Ca curve) to global cardiac performance (e.g., simulated ejection fraction). In an example, one or more embodiments can employ concepts of sensitivity analysis to compute both first-order (S1) and total sensitivity (ST) indices for select output features, based on a number of simulations (e.g., several thousands) accounting for combined variations of input parameters.

One or more embodiments can treat the hyperspace of parameters as occupying a regularly-shaped domain, and thus these embodiments, to enable sensitivity analysis, can choose a priori the boundaries of the hyperparameter space to be probed. In addition, one or more embodiments, when analyzing and using models (e.g., complex multi-scale models such as the 3-D FE models discussed above) can identify and omit, if necessary, parameter combinations for these models that yield results that are not useful, e.g., parameter combinations that can cause unsustainable blood pressure. Similarly, one or more embodiments can identify regions of the parameter spaces yielding admissible outputs, e.g., by determining a sensitivity index that can exclude sub-regions yielding outputs deemed as not useful for a particular inquiry.

While the minimization approach shown in Equation #5 above can be used by one or more embodiments of the low-order models described herein to solve, with few high-resolution runs, for the trained parameters corresponding, for example, to a left-ventricle geometry, to reduce the computational burden if needed, one or more embodiments can use a Gaussian process regression model to map the geometric parameters of the left ventricle (e.g., $\{R_b, L, Z, H, \Psi_0, e\}$) to the parameters of the a low-order model (e.g., $\{\alpha, \beta, \gamma, a, b, c, \mu_1, \mu_2\}$).

In one or more embodiments this regression model can be trained using a Latin hypercube that can sample anatomies uniformly distributed over the range of anatomies observed for a sampling of patients. Similar to the approach described above with FIG. 4 above, one or more embodiments can virtually "unload" the geometries assuming an end-diastolic stretch, and can perform congruency training for each geometry under several hemodynamic boundary conditions, e.g., the conditions discussed with Table #2 included above. One or more embodiments can assess an efficacy of the fitted regression model in learning the behavior of the low-order indices, by evaluating, for example, via cross-validation.

In an alternative approach used by one or more embodiments, the above-described training of low-order models by FE models can be reversed. In this example, low-order model behavior can be reconducted to an equivalent multiscale FE model by prior knowledge and congruency training similar to the congruency training described above with the description of FIG. 5.

Figure 6:
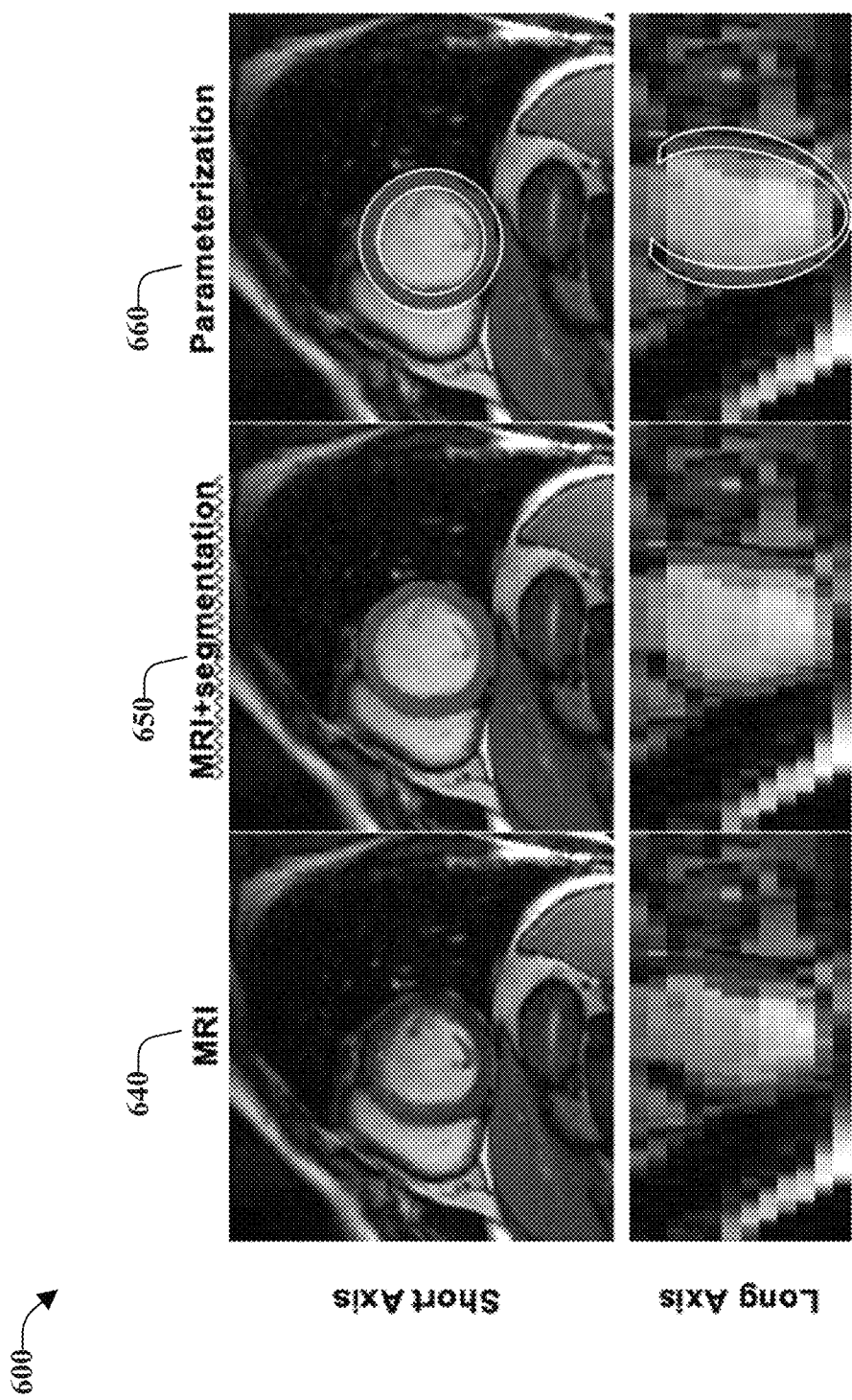
FIG. 6 is an example of segmentation of medical images in accordance with one or more embodiments described herein.
Figure 7:
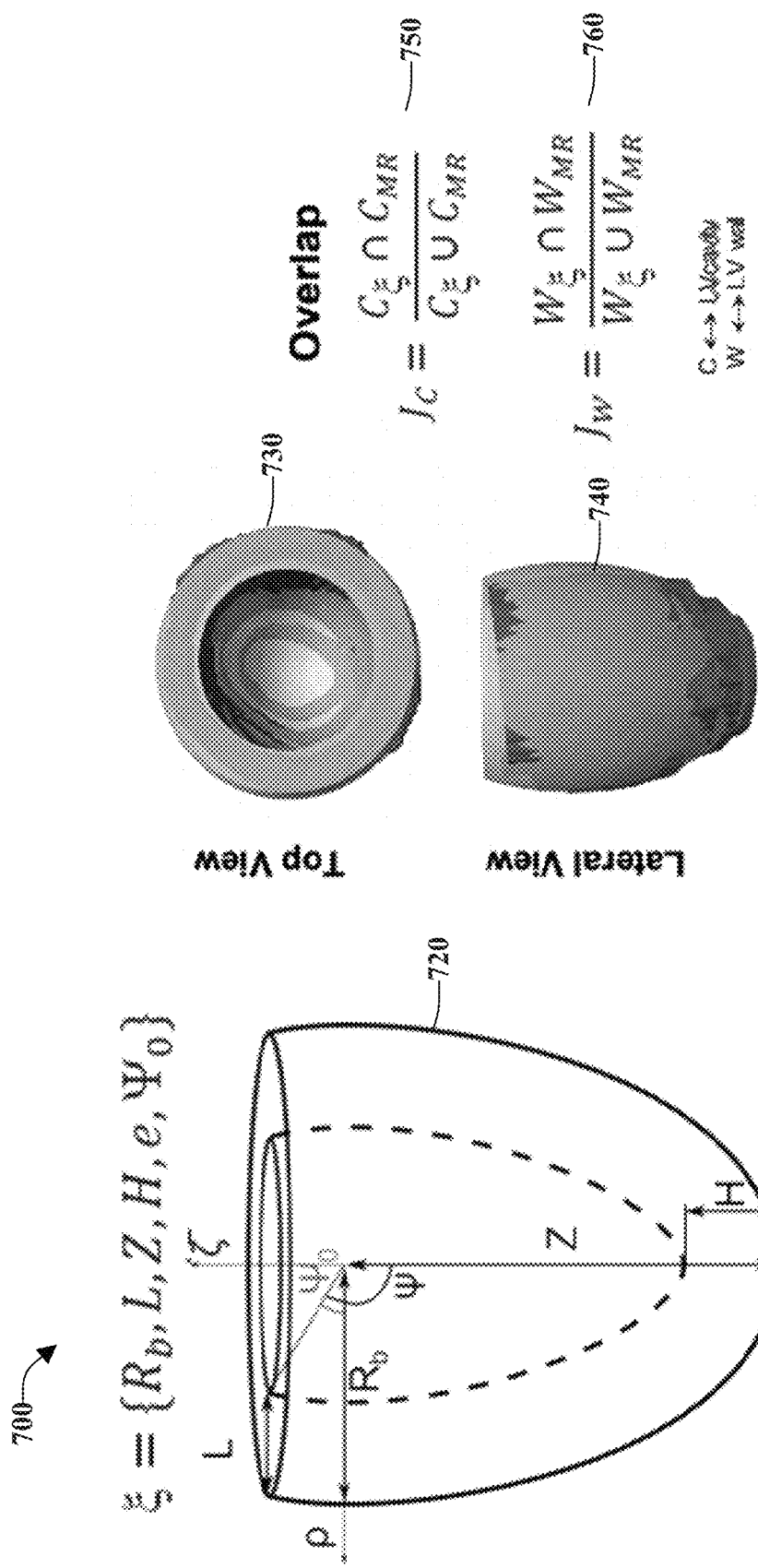
FIG. 7 is an example of results of the segmentation of medical images in accordance with one or more embodiments described herein.

FIGS. 6 and 7 depict an example that employs a low-order model to model, using medical images, a specific patient affected by cardiac pathologies in accordance with one or more embodiments described herein. Repetitive description of like elements and/or processes employed in respective embodiments is omitted for sake of brevity.

As shown in FIG. 6, in this example, inputs for the low-order model can include diagnostic data, e.g., data retrieved by one or more embodiments from medical imaging systems such as magnetic resonance imaging (MRI 640), cardiac echocardiography, and computed tomography (CT), as well as diagnostic assessments such as clinical reports compiled by operators analyzing the medical images (e.g., records retrieved by one or more embodiments from an electronic medical record database). Additionally, physiological signals (e.g., systolic and diastolic blood pressure) can be collected by one or more embodiments by different kinds of invasive/non-invasive sensors, and this data can be introduced to reduce uncertainty of predictions. Applied to specific patients, one or more embodiments can produce biomarkers that can be used to construct statistical models of disease progression that allow exploring potential outcomes of surgical and pharmaceutical interventions.

In 650, the MRI 640 images can be segmented by one or more embodiments by analyzing the MRI images to identify structures to be used by the low-order model. In 660, the identified segments can be parameterized for use as inputs for the low-order models, as discussed herein.

FIG. 7 is an example of results of segmentation and parameterization of a medical image that can be performed by one or more embodiments. For example, FIG. 7 depicts segmented results (e.g., 730 and 740) of a medical image that can be used to construct a parameterization 720 of the left ventricular geometry. As depicted, in this example, parametrization 720 can be an idealized truncated prolate spheroid, defined, for example, by 6 parameters: the outer radius at base, $R_b$, the length of the longitudinal semi-axis of the spheroid, $Z_b$, the ventricular wall thicknesses at base (L) and apex (H), respectively, the truncation angle, $\Psi_0$, and the sphericity/conicity of the spheroid, $\varepsilon$.

In this example, once the medical image is segmented and parameterized by one or more embodiments, parameter analysis and selection approaches described herein (e.g., with FIGS. 3-5 above) can be used to identify sets of parameters that correspond to the identified medical image segmentations. Equations 750 and 760 are sample equations that can be used by one or more embodiments with a low-order model and the values determined by parameterization 720.

Figure 8:
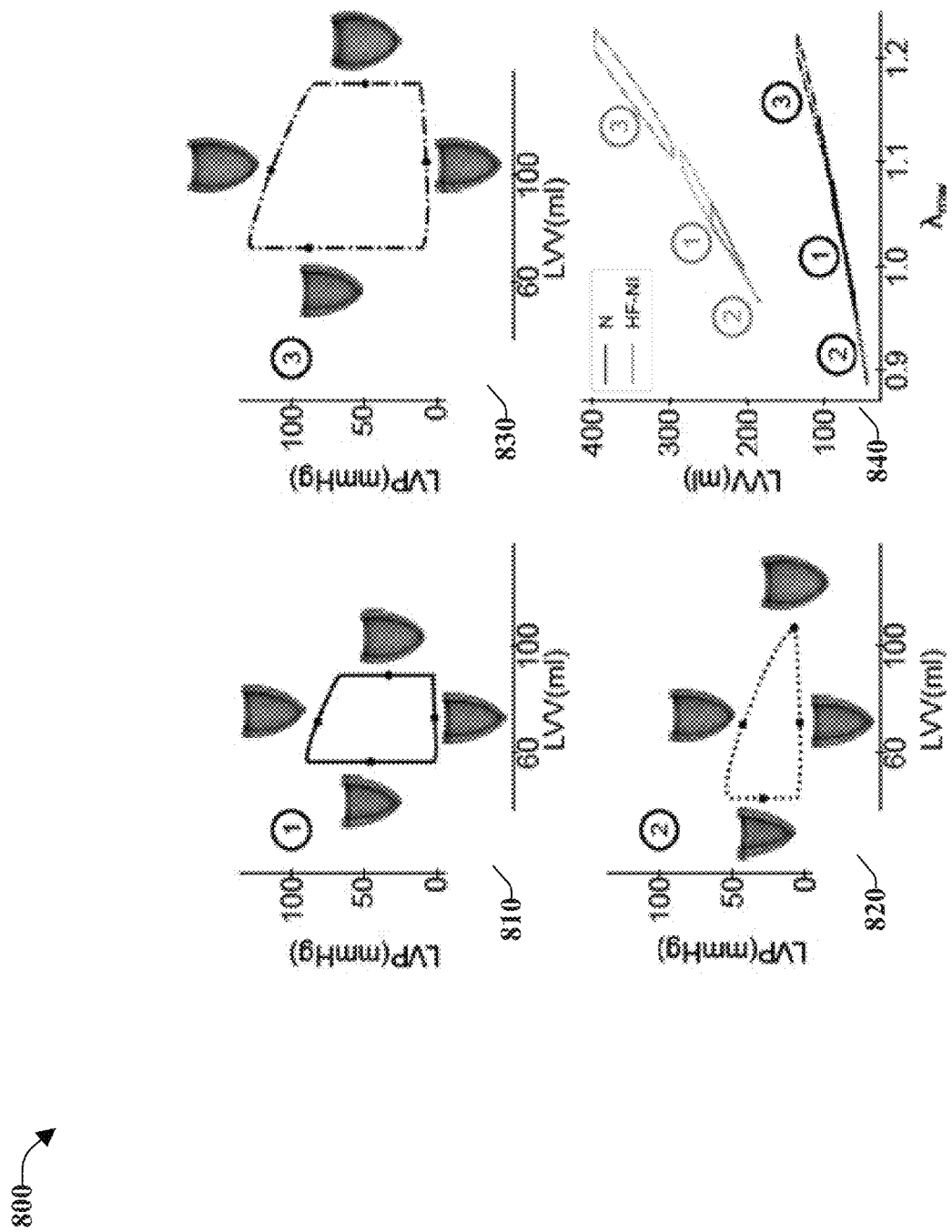
FIG. 8 illustrates an example of collected data of an operation of an entity used by one or more embodiments to populate parameters of a model of the entity.

FIG. 8 illustrates an example of collected data of an operation of an entity (e.g., the left ventricle) used by one or more embodiments to populate parameters of a model of the entity. Repetitive description of like elements and/or processes employed in respective embodiments is omitted for sake of brevity.

FIG. 8 depicts training simulations of left ventricle pressure volume loops, that can be used, for example, by one or more embodiments using congruency training, as described in FIGS. 3 and 5 above. These example training simulations can be used for example, by one or more embodiments, to train a low-order model to use a linear relationship between volume and midwall stretch in the fiber direction and a linear relationship between pressure and cellular tension. In examples: training simulation 810 yields an ejection fraction of 36% and maximum left ventricular pressure (LVP) of 90 mmHg, training simulation 820 shows higher EF and lower LVP that can be due, for example, to lower peripheral resistance, training simulation 830 shows a PV loop characterized by a significantly larger LVP during ejection, that can be driven, for example, by large atrial pressure. LVV traces 840 are plotted against corresponding midwall strains, and can reveal, for example, an approximately linear relationship over the large range of strains probed by training simulations 810, 820, and 830.

Figure 9:
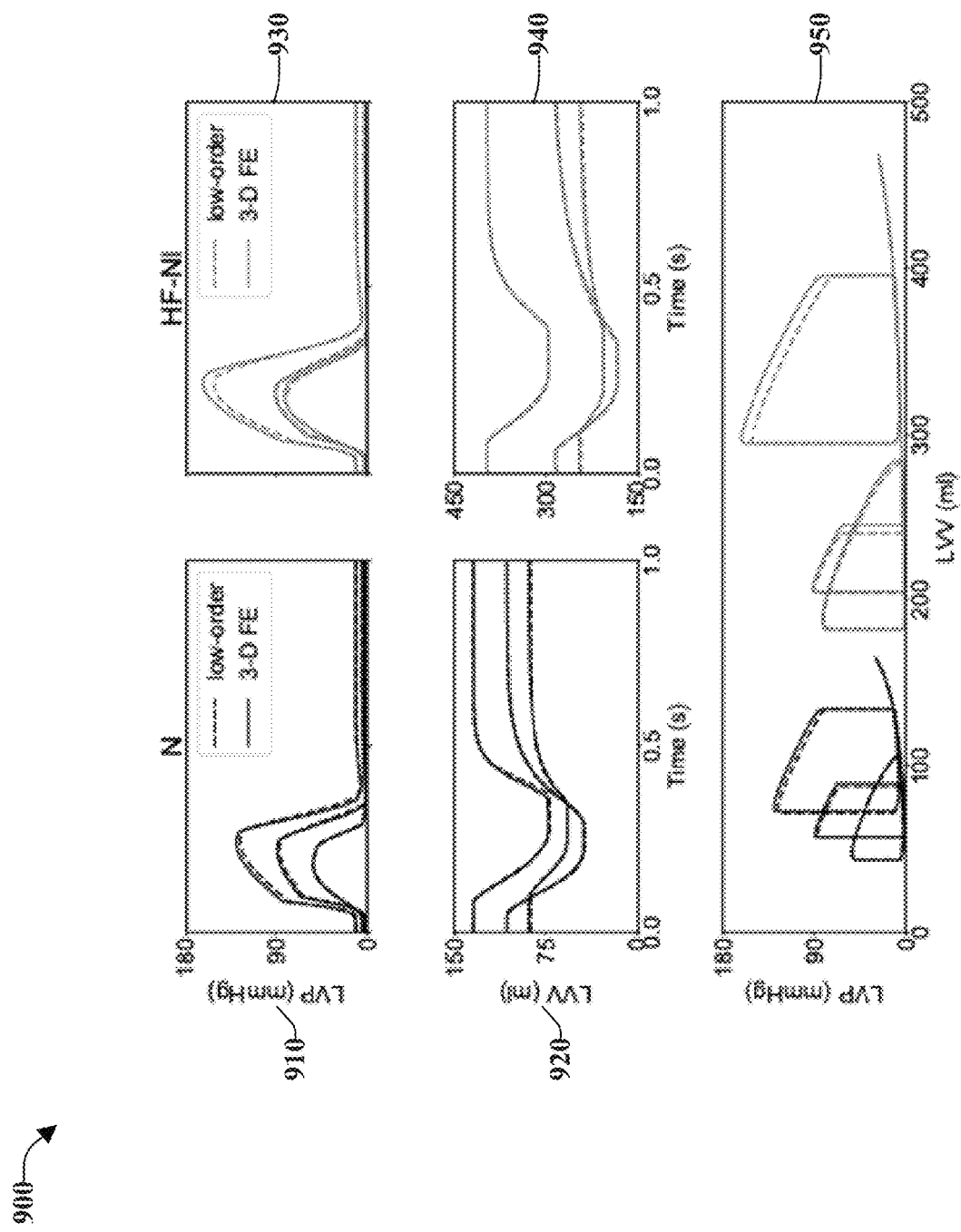
FIG. 9 illustrates an example of congruency training of a low-order model of passive and active behaviors of ventricular cardiac mechanics in accordance with one or more embodiments described herein.

FIG. 9 illustrates an example of congruency training, by one or more embodiments, of a low-order model of passive and active behaviors of ventricular cardiac mechanics, as described with FIG. 5 above. As depicted in charts 910-950, a level of congruency can be achieved based on the approaches discussed herein, e.g., as discussed above with FIG. 3, this congruency can be assessed based on threshold (e.g., satisfying a particular criterion above a threshold, e.g., similarity). One or more of the examples depicted in FIG. 9 show a level of similarity that can satisfy the criterion in one or more embodiments. For example, the dotted lines correspond to the results yielded by a low-order model trained by an FE model. As shown in FIG. 9, the dotted lines of the results of the low-order have a level of similarity to solid-line results of the FE model used. In one or more embodiments, the similarity depicted in charts 910-950 are an example of results that satisfy a threshold of similarity used by the one or more embodiments. Repetitive description of like elements and/or processes employed in respective embodiments is omitted for sake of brevity.

Figure 10:
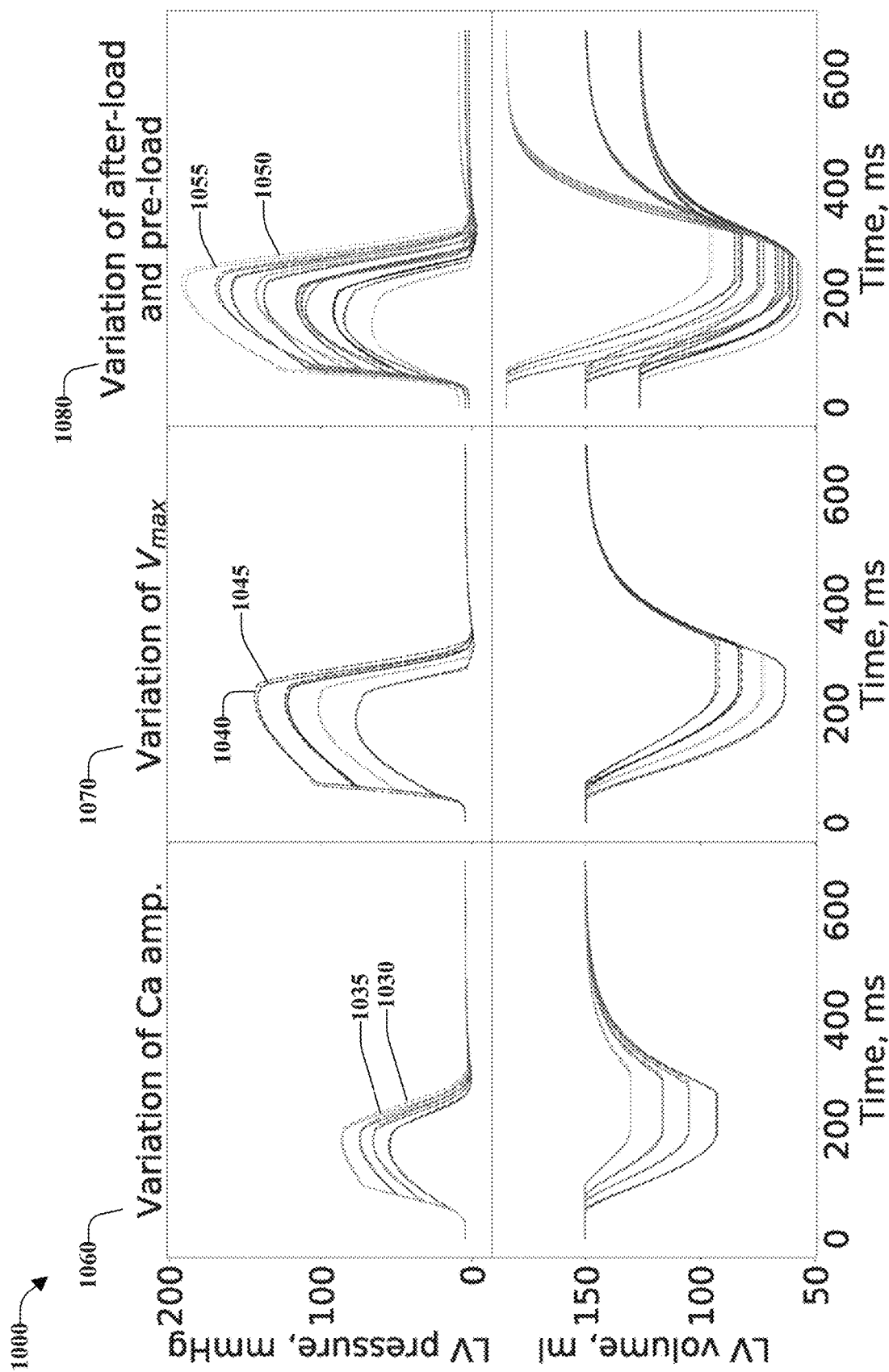
FIG. 10 is an example of a low-order model of cardiac mechanics compared to a 3-D finite element model of cardiac mechanics in accordance with one or more embodiments described herein.

FIG. 10 illustrates examples of correlation between a trained low-order model of cardiac mechanics and a 3-D finite element model of cardiac mechanics in accordance with one or more embodiments described herein. Repetitive description of like elements and/or processes employed in respective embodiments is omitted for sake of brevity.

FIG. 10 shows example outputs of the low-order models (dashed lines 1030, 1040, and 1050) obtained after opportune sizing of the transformations overlapped to the same global metrics simulated via high-resolution FE models (solid lines 1035, 1045, and 1055 respectively). Example comparisons between low-order models and FE models are shown for three example sets of simulated conditions that deviate from the conditions considered during training of the low-order model in this example, e.g., variation of calcium amplitude 1060, variation of maximal, no-load, velocity for the contractile element ($V_{max}$) 1070, and variation of afterload and pre-load values 1080. In this example, the low-order and FE models employ the same parameter values wherever possible, e.g., both for driving myocyte contraction and for the hemodynamic coupling.

Figure 11:
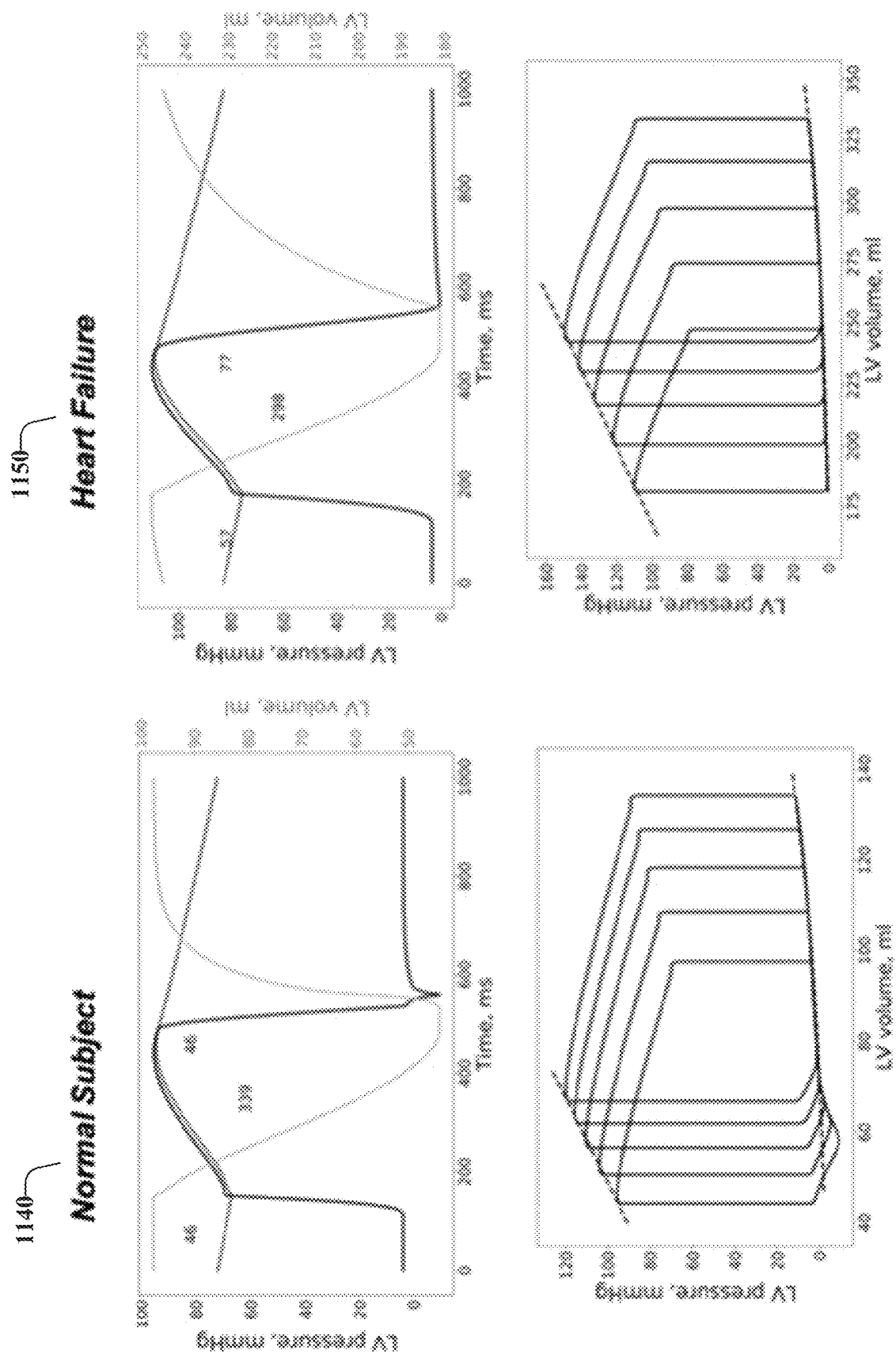
FIG. 11 is an example of results of transforming a low-order model of cardiac mechanics by a finite element model of cardiac mechanics in accordance with one or more embodiments described herein.

FIG. 11 is an example of results of training a low-order model of cardiac mechanics by a finite element model of cardiac mechanics in accordance with one or more embodiments described herein. The charts shown depict example of the analysis described in FIG. 4 above, where a trained low-order model can reproduce characteristics of behavior of a \normal subject (e.g., chart 1140) and a subject that is in a condition of heart failure (e.g., chart 1150). In one or more embodiments, the congruency threshold criteria discussed with FIG. 9 above can be used to assess the similarity between measured results from the low-order model, and the patterns depicted in FIG. 11. In one or more embodiments, exceeding a threshold level of similarity between collected results from a patient and the heart failure example chart 1150 above can indicate a possibility of a heart failure condition. Repetitive description of like elements and/or processes employed in respective embodiments is omitted for sake of brevity.

Figure 12:
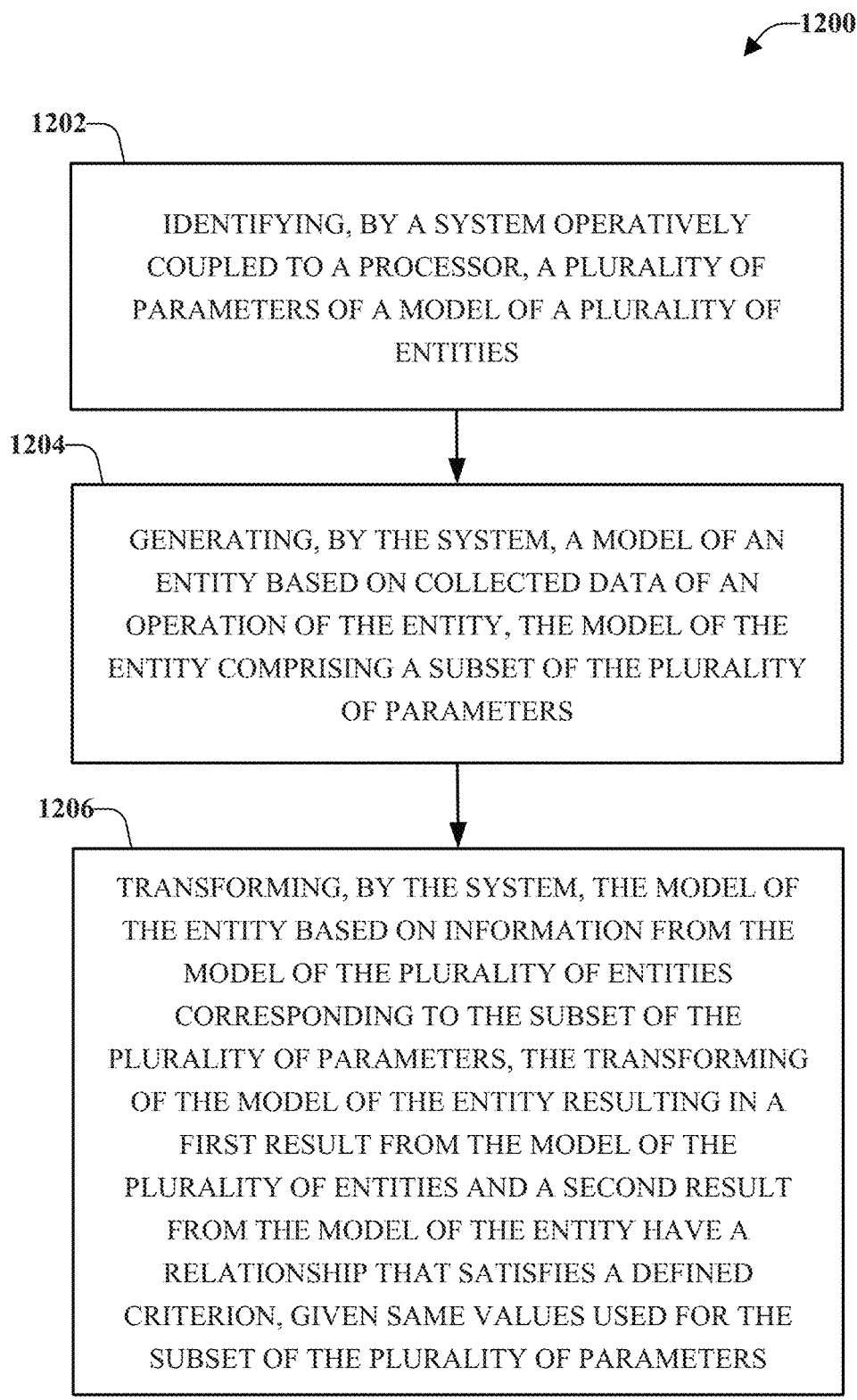
FIG. 12 illustrates a flow diagram of an example, non-limiting computer-implemented method that can facilitate transforming a model of an entity based on information from a model of a plurality of entities based on parameters in accordance with one or more embodiments described herein.

FIG. 12 illustrates a block diagram of an example, non-limiting computer implemented method 1200 that can facilitate the transformation of one model by another model in accordance with one or more embodiments described herein.

At 1202, the method includes identifying, by a system (e.g., system 150) operatively coupled to a processor (e.g., processing component 160), a plurality of parameters (e.g., plurality of parameters 227) of a model of a plurality of entities (e.g., model of a plurality of entities 225).

At 1204, the method includes generating, by the system, a model of an entity (e.g., generate a model of the entity in block 220) based on collected data of an operation of the entity (e.g., collected data of an operation of the entity), wherein the model of the entity comprises a subset of the plurality of parameters (e.g., identified subset of the plurality of parameters 222).

At 1206, the method includes transforming, by the system, the model of the entity (e.g., transform the model of the entity in block 230) based on information from the model of the plurality of entities corresponding to the subset of the plurality of parameters, wherein the transforming the model of the entity results (e.g., transformed model of the entity 232) in a first result from the model of the plurality of entities (e.g., model of the plurality of entities 225) and a second result from the model of the entity (e.g., result 242) have a relationship that satisfies a defined criterion, given same values used for the subset of the plurality of parameters. Repetitive description of like elements and/or processes employed in respective embodiments is omitted for sake of brevity.

Figure 13:
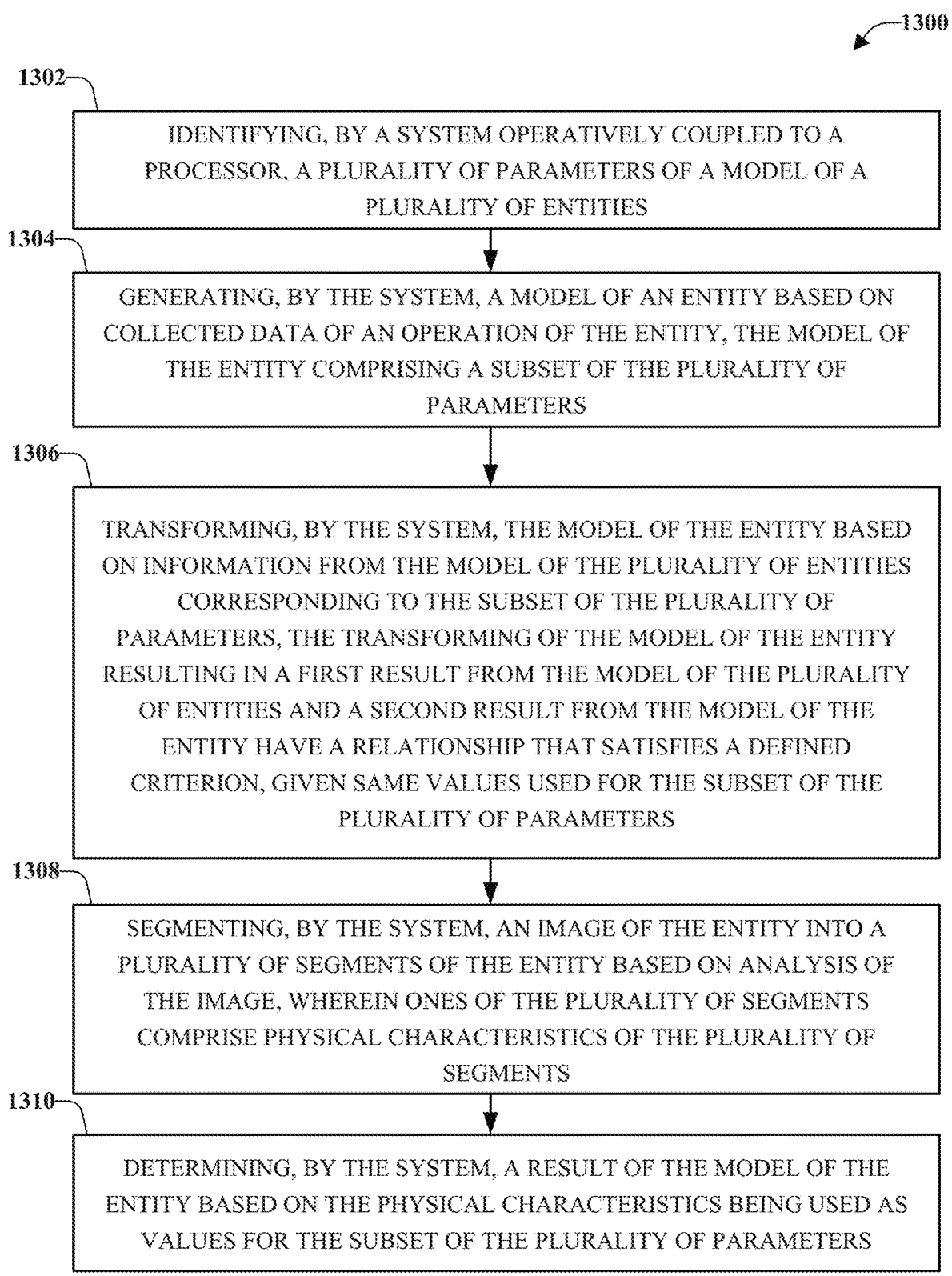
FIG. 13 illustrates a flow diagram of an example, non-limiting computer-implemented method that can facilitate transforming a model of an entity based on information from a model of a plurality of entities based on parameters in accordance with one or more embodiments described herein.

FIG. 13 illustrates a block diagram of an example, non-limiting computer implemented method 1300 that can facilitate the transformation of one model by another model in accordance with one or more embodiments described herein. Repetitive description of like elements and/or processes employed in respective embodiments is omitted for sake of brevity.

At 1302, the method includes identifying, by a system (e.g., system 150) operatively coupled to a processor (e.g., processing component 160), a plurality of parameters (e.g., plurality of parameters 227) of a model of a plurality of entities (e.g., model of a plurality of entities 225).

At 1304, the method includes generating, by the system, a model of an entity (e.g., generate a model of the entity in block 220) based on collected data of an operation of the entity (e.g., collected data of an operation of the entity), wherein the model of the entity comprises a subset of the plurality of parameters (e.g., identified subset of the plurality of parameters 222).

At 1306, the method includes transforming, by the system, the model of the entity (e.g., transform the model of the entity in block 230) based on information from the model of the plurality of entities corresponding to the subset of the plurality of parameters, wherein the transforming the model of the entity results (e.g., transformed model of the entity 232) in a first result from the model of the plurality of entities (e.g., model of the plurality of entities 225) and a second result from the model of the entity (e.g., result 242) have a relationship that satisfies a defined criterion, given same values used for the subset of the plurality of parameters.

At 1308, the method includes segmenting, by the system, an image of the entity (e.g., MRI 640 depicts an image of a heart) into a plurality of segments of the entity (e.g., MRI 640 is segmented at 650) based on analysis of the image (e.g., analysis of MRI 640), wherein ones of the plurality of segments comprise physical characteristics of the plurality of segments.

At 1310, the method includes determining, by the system, a result of the transformed model of the entity (e.g., low-order model 540) based on the physical characteristics being used as values for the subset of the plurality of parameters (e.g., at 660, the identified segments of MRI 640 can be parameterized and used with low-order model 540 as depicted in FIG. 7).

Figure 14:
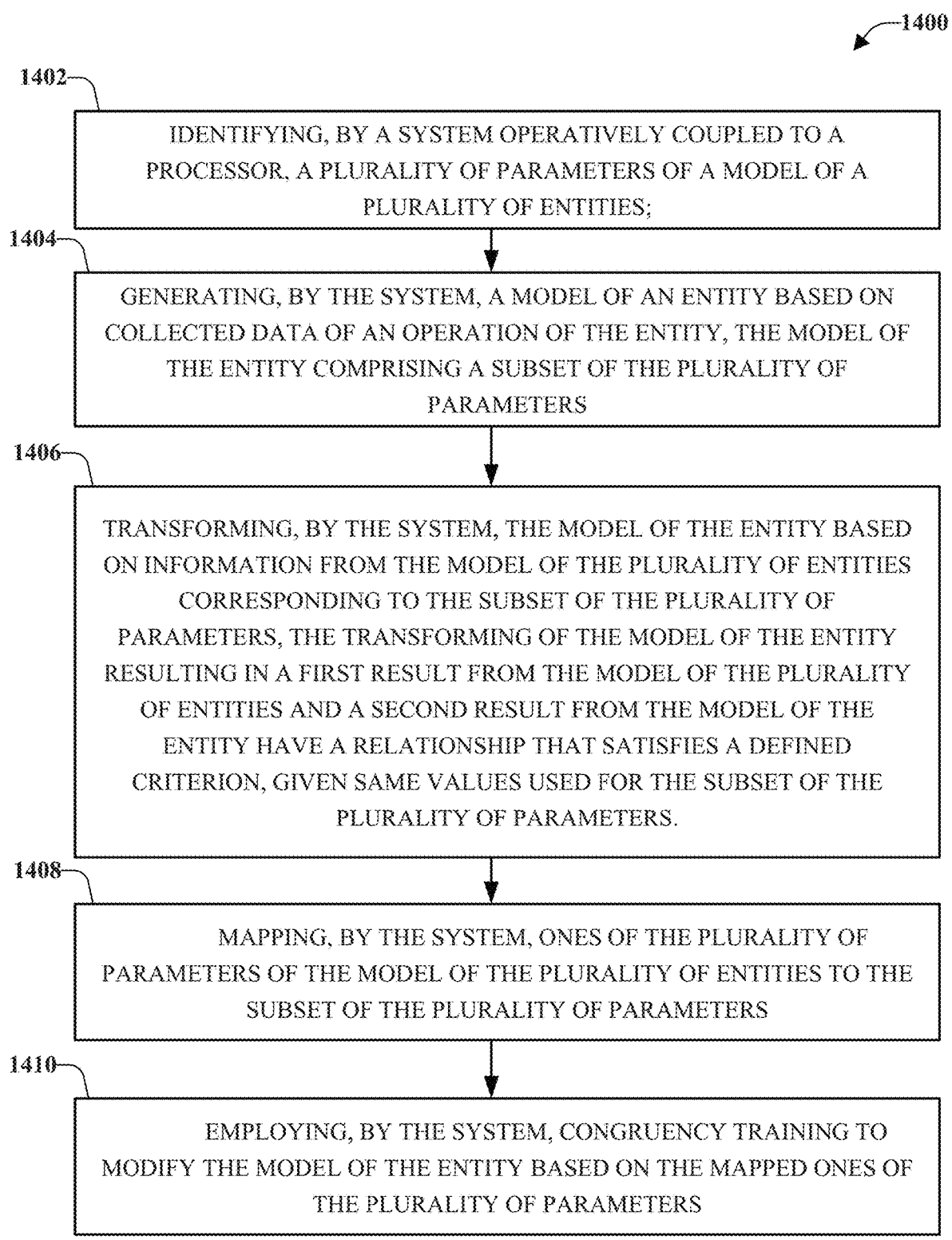
FIG. 14 illustrates a flow diagram of an example, non-limiting computer-implemented method that can facilitate transforming a model of an entity based on information from a model of a plurality of entities based on parameters in accordance with one or more embodiments described herein.

FIG. 14 illustrates a block diagram of an example, non-limiting computer implemented method 1400 that can facilitate the transformation of one model by another model in accordance with one or more embodiments described herein. Repetitive description of like elements and/or processes employed in respective embodiments is omitted for sake of brevity.

At 1402, the method includes identifying, by a system (e.g., system 150) operatively coupled to a processor (e.g., processing component 160), a plurality of parameters (e.g., plurality of parameters 227) of a model of a plurality of entities (e.g., model of a plurality of entities 225).

At 1404, the method includes generating, by the system, a model of an entity (e.g., generate a model of the entity in block 220) based on collected data of an operation of the entity (e.g., collected data of an operation of the entity), wherein the model of the entity comprises a subset of the plurality of parameters (e.g., identified subset of the plurality of parameters 222).

At 1406, the method includes transforming, by the system, the model of the entity (e.g., transform the model of the entity in block 230) based on information from the model of the plurality of entities corresponding to the subset of the plurality of parameters, wherein the transforming the model of the entity results (e.g., transformed model of the entity 232) in a first result from the model of the plurality of entities (e.g., model of the plurality of entities 225) and a second result from the model of the entity (e.g., result 242) have a relationship that satisfies a defined criterion, given same values used for the subset of the plurality of parameters.

At 1408, the method includes mapping, by the system, ones of the plurality of parameters of the model of the plurality of entities to the subset of the plurality of parameters. For example, FIG. 7 depicts the mapping of parameters determined by analyzing the segments of MRI 640 to parameters of low-order model 540.

At 1410, the method includes employing, by the system, congruency training to modify the model of the entity based on the mapped ones of the plurality of parameters. For example, FIG. 5 depicts employing congruency training 590 to modify (i.e., train) low-order model 540 using parameters mapped from global outputs 560.

For simplicity of explanation, the computer-implemented methodologies are depicted and described as a series of acts. It is to be understood and appreciated that the subject innovation is not limited by the acts illustrated and/or by the order of acts, for example acts can occur in various orders and/or concurrently, and with other acts not presented and described herein. Furthermore, not all illustrated acts can be required to implement the computer-implemented methodologies in accordance with the disclosed subject matter. In addition, those skilled in the art will understand and appreciate that the computer-implemented methodologies could alternatively be represented as a series of interrelated states via a state diagram or events. Additionally, it should be further appreciated that the computer-implemented methodologies disclosed hereinafter and throughout this specification are capable of being stored on an article of manufacture to facilitate transporting and transferring such computer-implemented methodologies to computers. The term article of manufacture, as used herein, is intended to encompass a computer program accessible from any computer-readable device or storage media.

Figure 15:
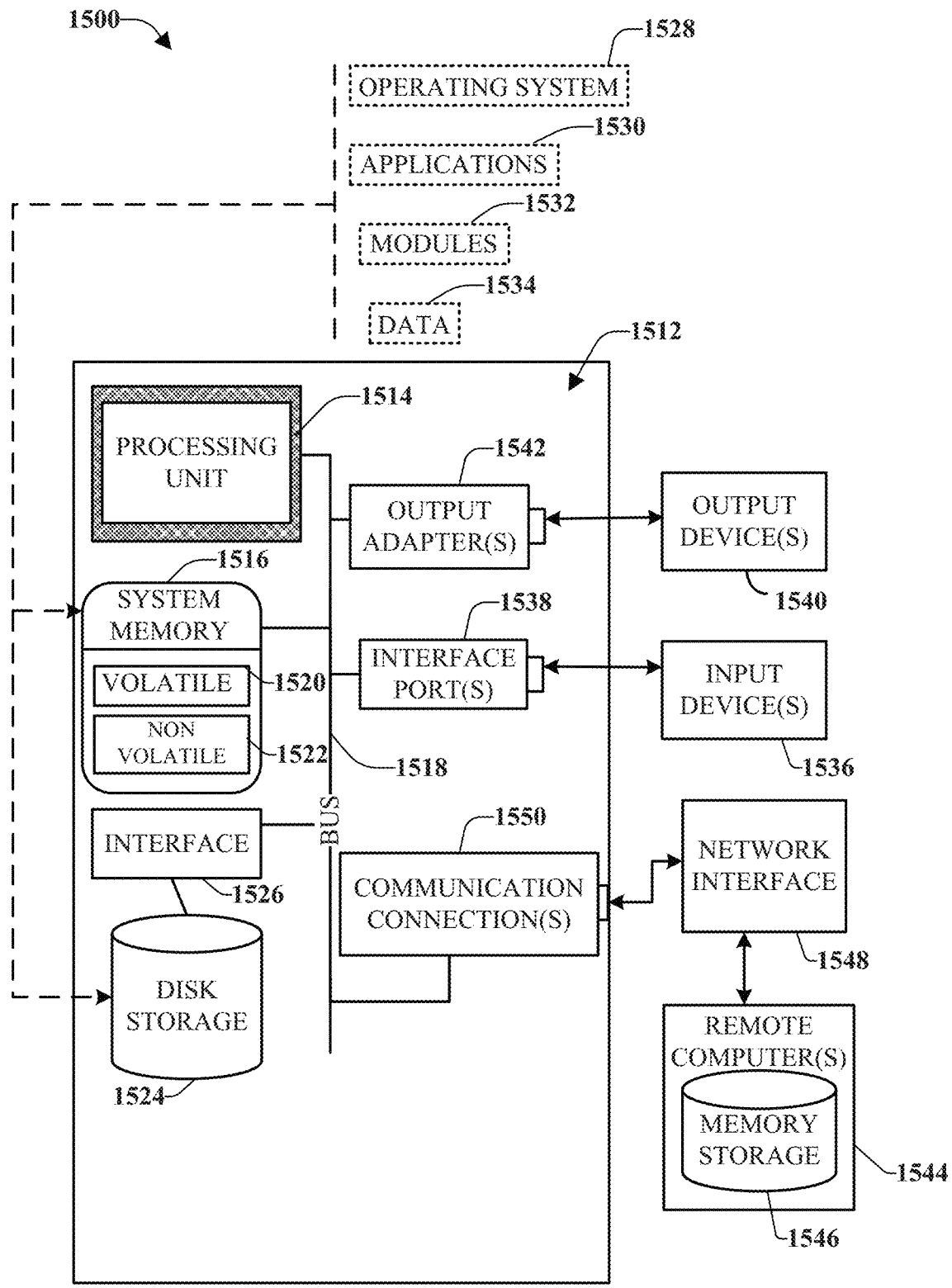
FIG. 15 illustrates a block diagram of an example, non-limiting operating environment in which one or more embodiments described herein can be facilitated.

In FIG. 15, in order to provide a context for the various aspects of the disclosed subject matter, provides a general description of a suitable environment in which the various aspects of the disclosed subject matter can be implemented. FIG. 15 illustrates a block diagram of an example, non-limiting operating environment in which one or more embodiments described herein can be facilitated. Repetitive description of like elements and/or processes employed in other embodiments described herein is omitted for sake of brevity.

With reference to FIG. 15, a suitable operating environment 1500 for implementing various aspects of this disclosure can also include a computer 1512. The computer 1512 can also include a processing unit 1514, a system memory 1516, and a system bus 1518. The system bus 1518 couples system components including, but not limited to, the system memory 1516 to the processing unit 1514. The processing unit 1514 can be any of various available processors. Dual microprocessors and other multiprocessor architectures also can be employed as the processing unit 1514. The system bus 1518 can be any of several types of bus structure(s) including the memory bus or memory controller, a peripheral bus or external bus, and/or a local bus using any variety of available bus architectures including, but not limited to, Industrial Standard Architecture (ISA), Micro-Channel Architecture (MSA), Extended ISA (EISA), Intelligent Drive Electronics (IDE), VESA Local Bus (VLB), Peripheral Component Interconnect (PCI), Card Bus, Universal Serial Bus (USB), Advanced Graphics Port (AGP), Firewire (IEEE 1394), and Small Computer Systems Interface (SCSI).

The system memory 1516 can also include volatile memory 1520 and nonvolatile memory 1522. The basic input/output system (BIOS), containing the basic routines to transfer information between elements within the computer 1512, such as during start-up, is stored in nonvolatile memory 1522. Computer 1512 can also include removable/non-removable, volatile/non-volatile computer storage media. FIG. 15 illustrates, for example, a disk storage 1524. Disk storage 1524 can also include, but is not limited to, devices like a magnetic disk drive, floppy disk drive, tape drive, Jaz drive, Zip drive, LS-100 drive, flash memory card, or memory stick. The disk storage 1524 also can include storage media separately or in combination with other storage media. To facilitate connection of the disk storage 1524 to the system bus 1518, a removable or non-removable interface is typically used, such as interface 1526. FIG. 15 also depicts software that acts as an intermediary between users and the basic computer resources described in the suitable operating environment 1500. Such software can also include, for example, an operating system 1528. Operating system 1528, which can be stored on disk storage 1524, acts to control and allocate resources of the computer 1512.

System applications 1530 take advantage of the management of resources by operating system 1528 through program modules 1532 and program data 1534, e.g., stored either in system memory 1516 or on disk storage 1524. It is to be appreciated that this disclosure can be implemented with various operating systems or combinations of operating systems. A user enters commands or information into the computer 1612 through input device(s) 1536. Input devices 1536 include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processing unit 1514 through the system bus 1518 via interface port(s) 1538. Interface port(s) 1538 include, for example, a serial port, a parallel port, a game port, and a universal serial bus (USB). Output device(s) 1540 use some of the same type of ports as input device(s) 1536. Thus, for example, a USB port can be used to provide input to computer 1512, and to output information from computer 1512 to an output device 1540. Output adapter 1542 is provided to illustrate that there are some output devices 1540 like monitors, speakers, and printers, among other output devices 1540, which require special adapters. The output adapters 1542 include, by way of illustration and not limitation, video and sound cards that provide a means of connection between the output device 1540 and the system bus 1518. It should be noted that other devices and/or systems of devices provide both input and output capabilities such as remote computer(s) 1544.

Computer 1512 can operate in a networked environment using logical connections to one or more remote computers, such as remote computer(s) 1544. The remote computer(s) 1544 can be a computer, a server, a router, a network PC, a workstation, a microprocessor based appliance, a peer device or other common network node and the like, and typically can also include many or all of the elements described relative to computer 1512. For purposes of brevity, only a memory storage device 1546 is illustrated with remote computer(s) 1544. Remote computer(s) 1544 is logically connected to computer 1512 through a network interface 1548 and then physically connected via communication connection 1550. Network interface 1548 encompasses wire and/or wireless communication networks such as local-area networks (LAN), wide-area networks (WAN), cellular networks, etc. LAN technologies include Fiber Distributed Data Interface (FDDI), Copper Distributed Data Interface (CDDI), Ethernet, Token Ring and the like. WAN technologies include, but are not limited to, point-to-point links, circuit switching networks like Integrated Services Digital Networks (ISDN) and variations thereon, packet switching networks, and Digital Subscriber Lines (DSL). Communication connection(s) 1550 refers to the hardware/ software employed to connect the network interface 1548 to the system bus 1518. While communication connection 1550 is shown for illustrative clarity inside computer 1512, it can also be external to computer 1512. The hardware/software for connection to the network interface 1548 can also include, for exemplary purposes only, internal and external technologies such as, modems including regular telephone grade modems, cable modems and DSL modems, ISDN adapters, and Ethernet cards.

Figure 16:
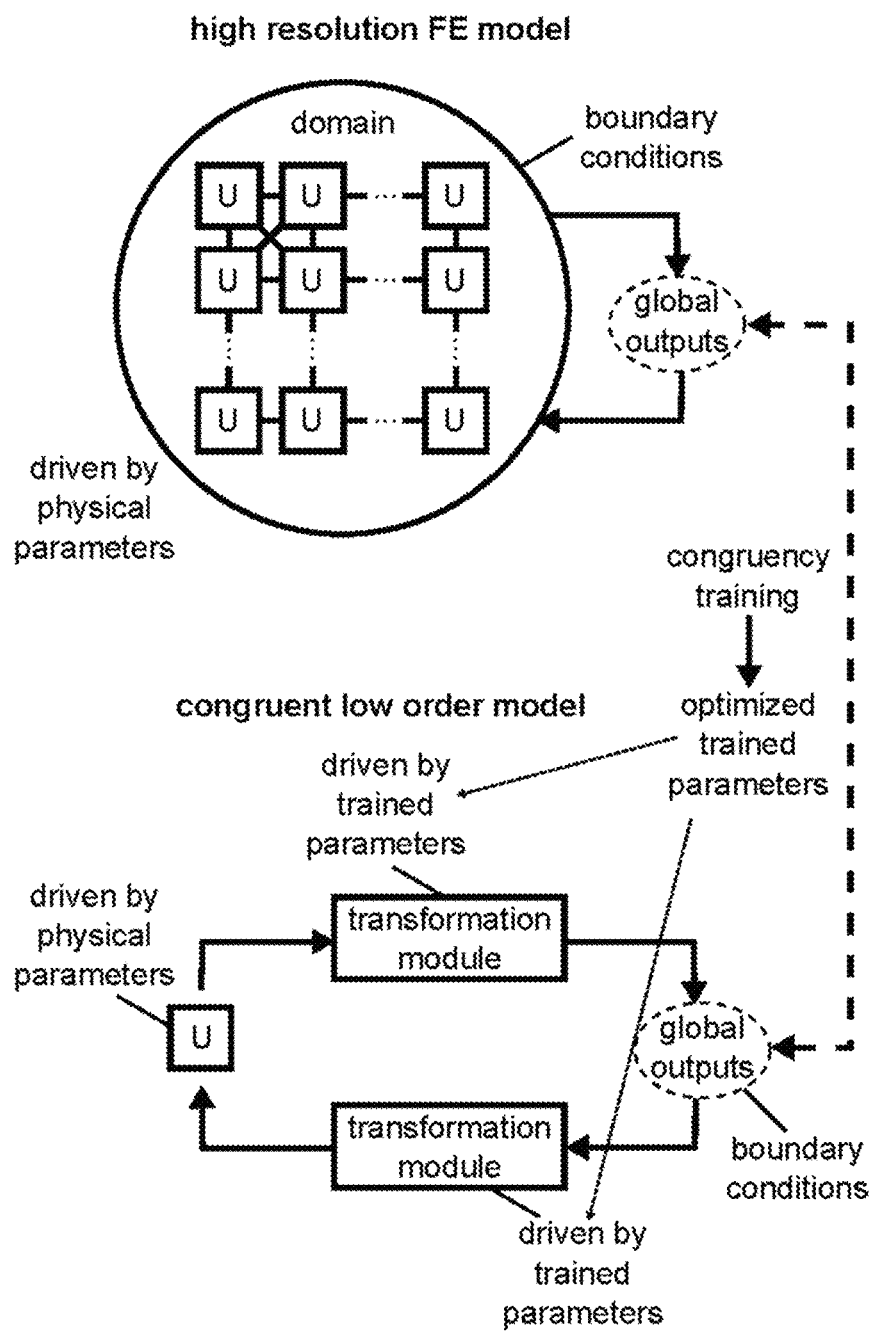
FIGS. 16-22 illustrate additional details of one or more embodiments described herein.

FIG. 16 depicts and embodiment where a high-resolution FE model is a multi-unit model that can simulate the behavior of several interconnected units (U) operating under imposed boundary conditions to generate global outputs of interest. Repetitive description of like elements and/or processes employed in respective embodiments is omitted for sake of brevity.

In one or more embodiments, the high-resolution multi-unit model behavior can be modulated by physical parameters that can be inferred from experimental measurements (e.g., medical imaging, electronic medical reports, wearable sensors, physical measurements). As shown in this embodiment, a low-order model can be a congruent model built to cut complexity and save computational costs of simulations. The low-order model can require modeling of just one unit coupled to global outputs via transformation modules. The unit behavior can be modulated by physical parameters similar to those used in the high-resolution FE models, while the transformation modules can rely on trained parameters that do not have a direct physical meaning. While physical parameters can be measured experimentally, optimal values for the trained parameters can be obtained via congruency training, a procedure that can maximize the match between global outputs of the high-resolution and low-order models.

Figure 17:
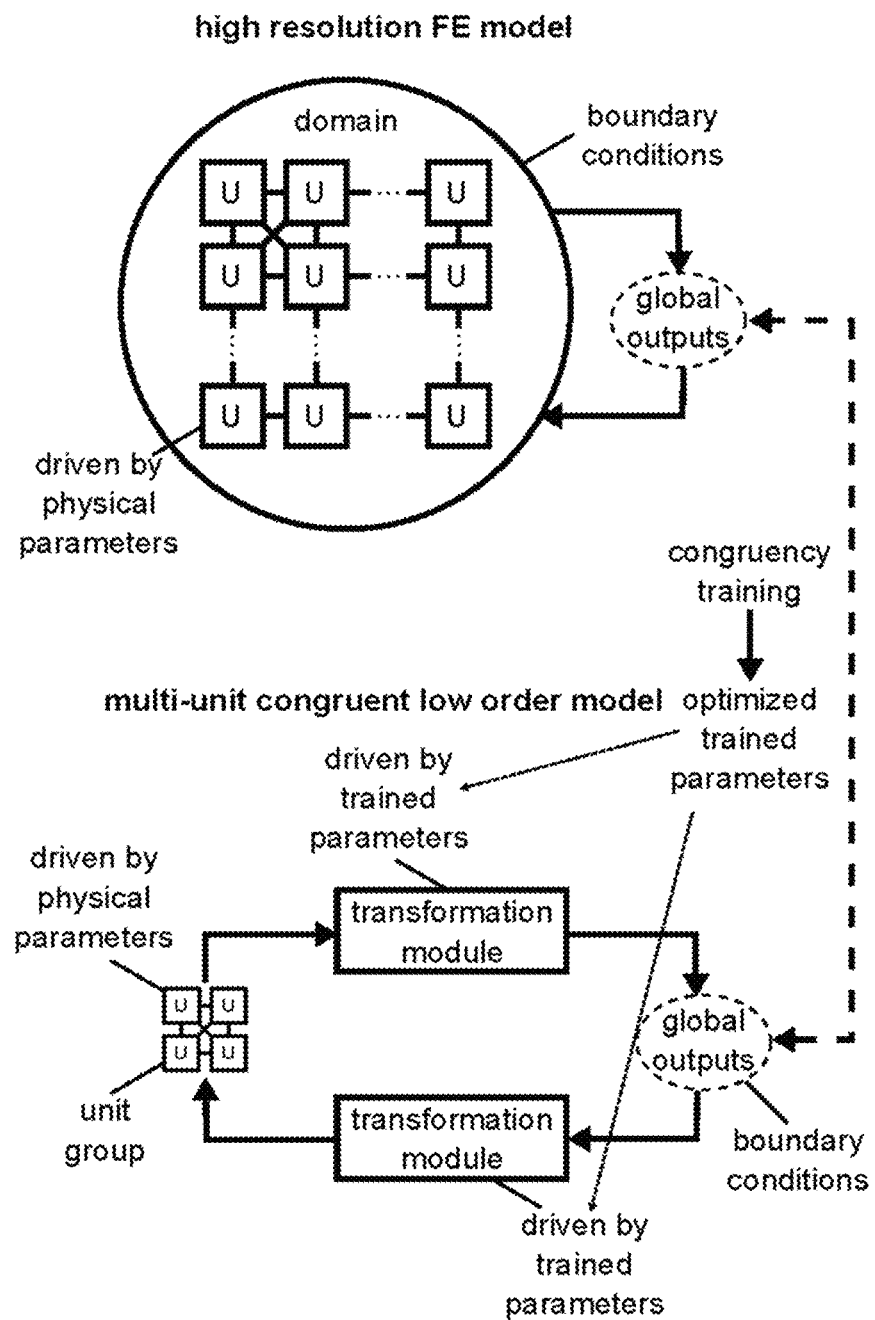

FIG. 17 depicts an embodiment with a group unit. This example is similar to the embodiment depicted in FIG. 16, but in this example, the low-order model can include includes a few interconnected units (e.g., a group unit) rather than just an isolated one as shown in FIG. 16. Repetitive description of like elements and/or processes employed in respective embodiments is omitted for sake of brevity.

Figure 18:
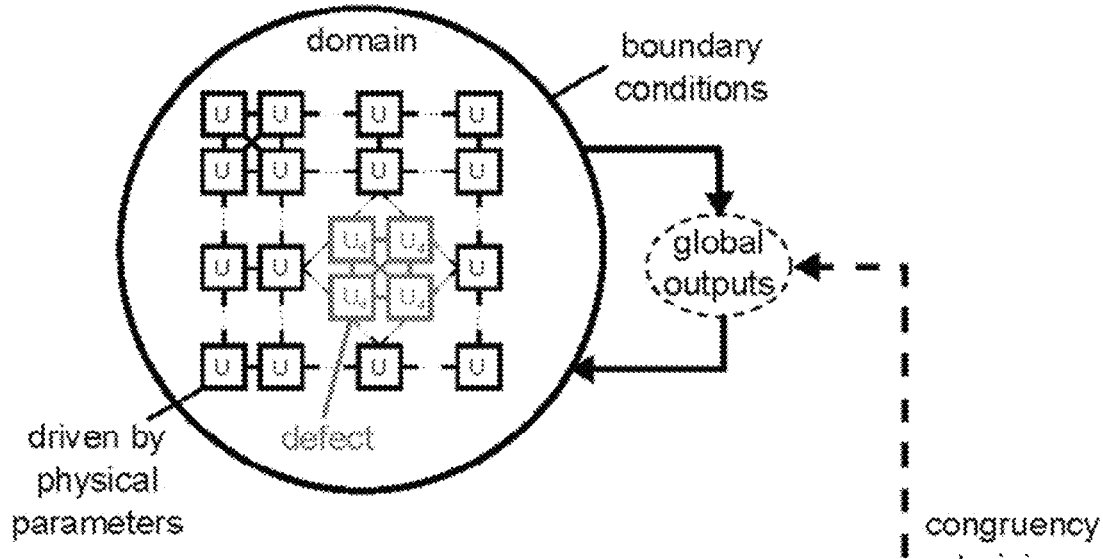
Figure 18:
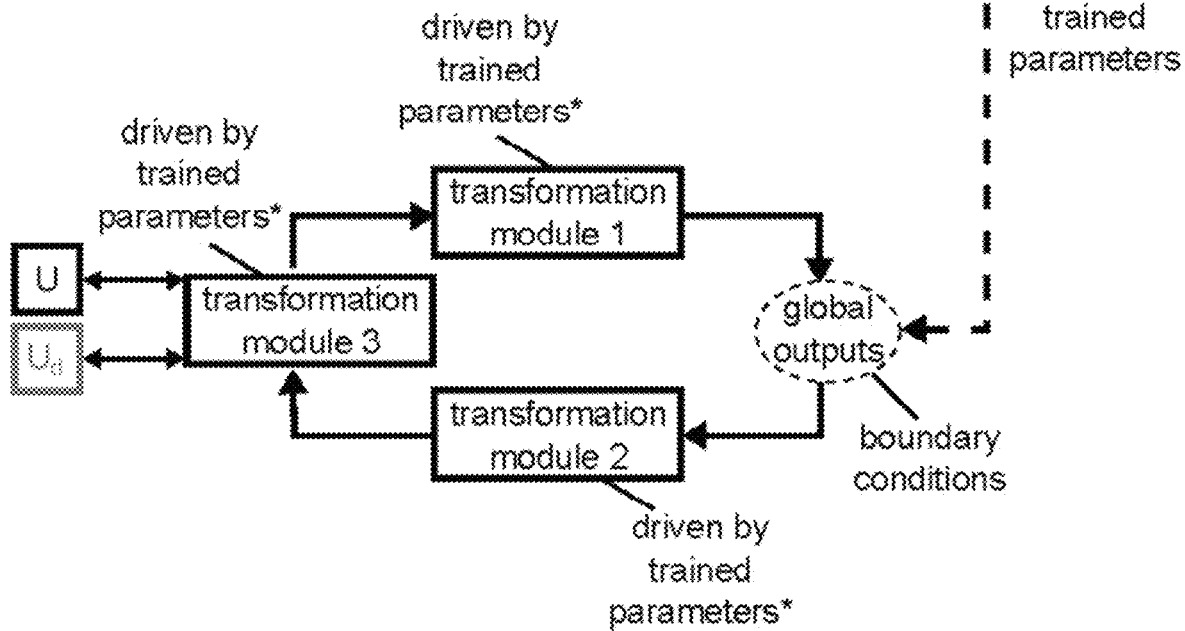

FIG. 18 depicts an embodiment where the high-resolution FE model accounts for a localized defect (e.g., a region behaving differently). In this example, similar to the example shown in FIG. 16, the embodiment can account for a defect in a model used by the embodiment. Repetitive description of like elements and/or processes employed in respective embodiments is omitted for sake of brevity.

In this example, the defect can be modeled as one or more subgroups of interconnected units ($U_d$) that can exhibit different behavior (e.g., due to different modeling formulation or to different parameters) affecting nearby coupled units and ultimately global outputs. In the embodiment depicted, the low-order model can capture the defect behavior by modeling both standard (U) and defective ($U_d$) units, which can be linked via an additional transformation module to the transformation modules coupled to the global outputs. In this approach, by maximizing a match between global outputs of high resolution and low-order models, the parameters trained via congruency training can modulate the role of transformations, e.g., accounting for the effect of the defect in the FE model at a reduced computational cost and cutting complexity.

Figure 19:
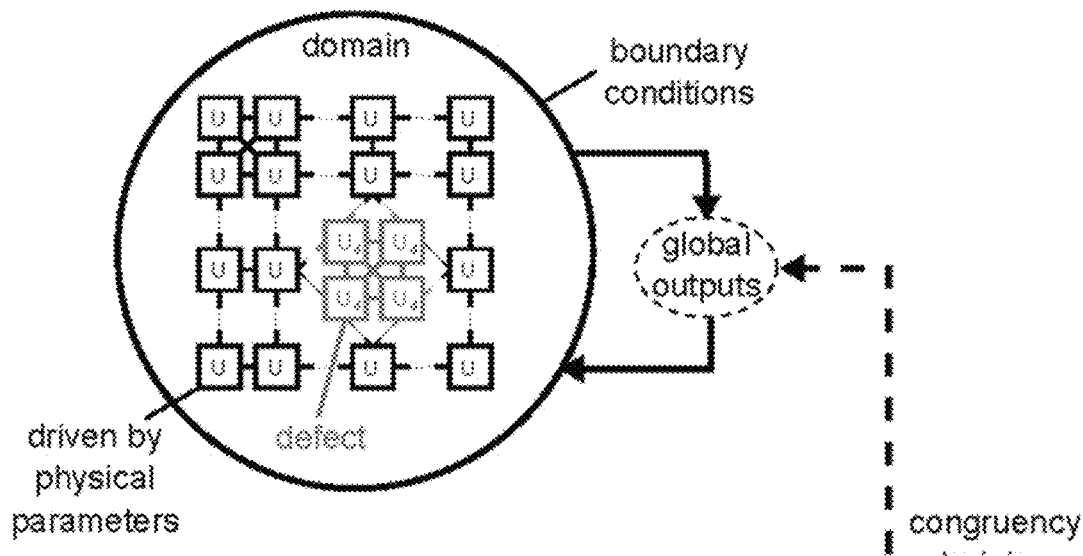
Figure 19:
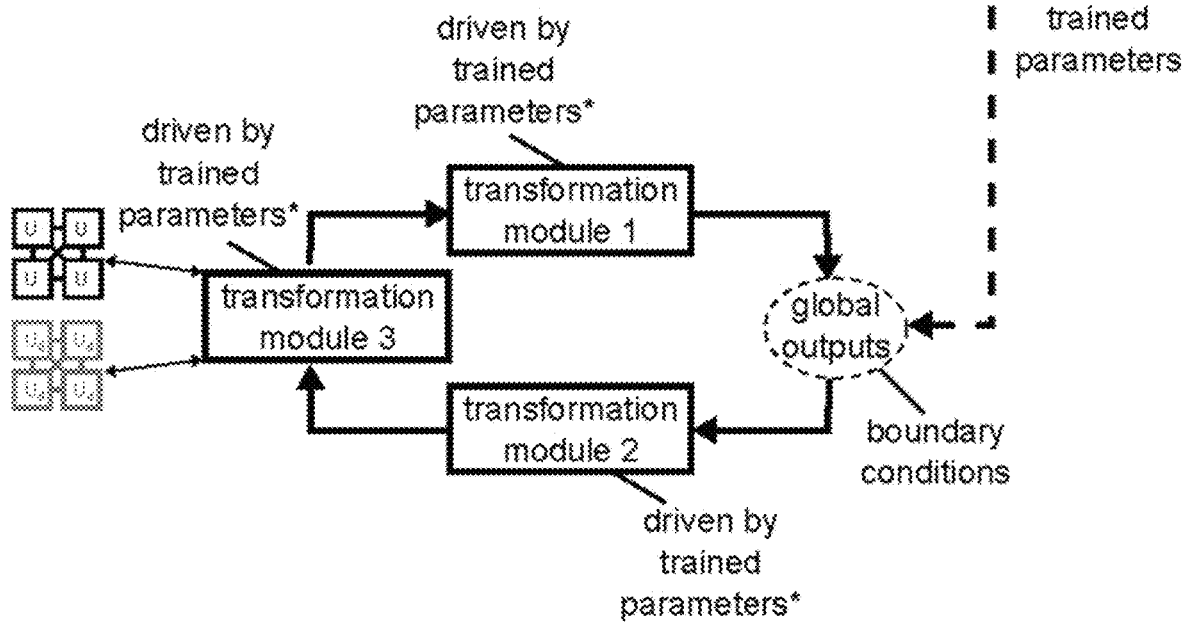

FIG. 19 depicts an embodiment where the high-resolution FE model accounts for a localized defect (e.g., a region behaving differently, as shown in FIG. 18). As shown in this example, the low-order model can include groups of interconnected units with standard and defective behavior. Repetitive description of like elements and/or processes employed in respective embodiments is omitted for sake of brevity.

Figure 20:
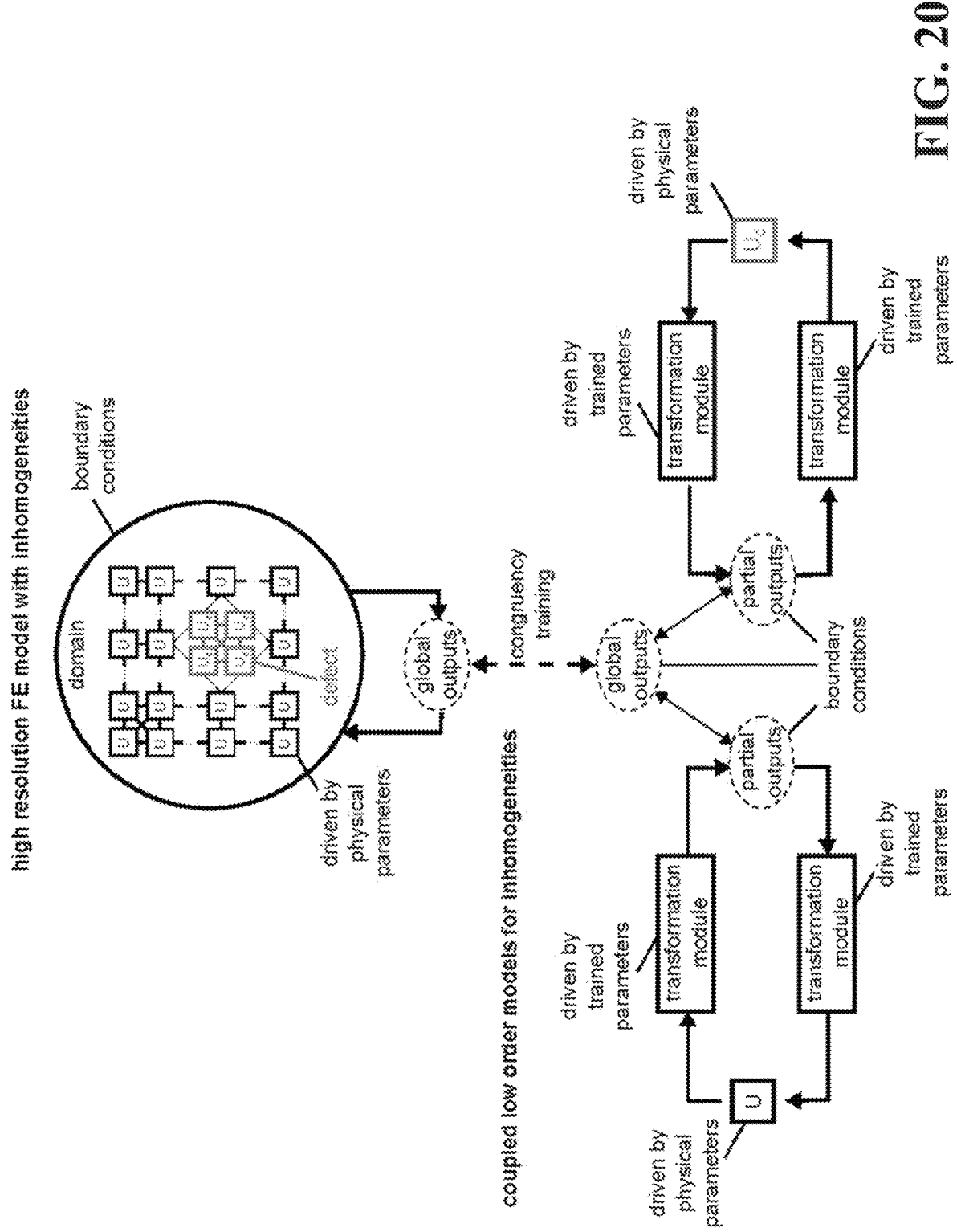

FIG. 20 depicts an embodiment similar to FIG. 18, but in this example, the model behavior with a defect can include two partial low-order models for the standard and defect behaviors. In this example, coupling between low-order models can occur via the global outputs, which can also affect and be affected by boundary conditions. Repetitive description of like elements and/or processes employed in respective embodiments is omitted for sake of brevity.

Figure 21:
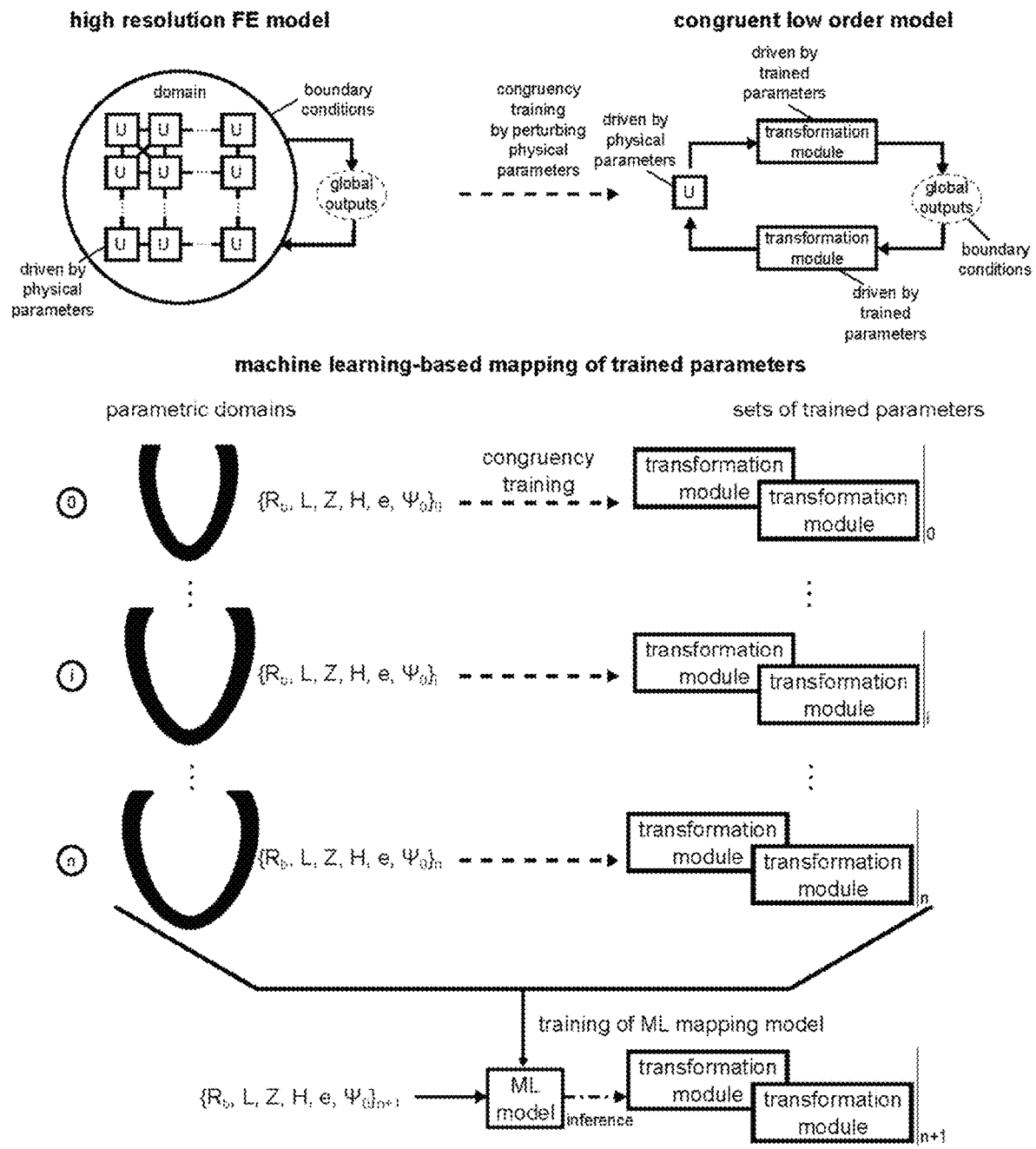

FIG. 21 depicts a machine learning model of congruency training that can be used by one or more embodiments. Shown at the top of the figure, congruency training can optimize parameters of the transformation modules by maximizing match of global outputs over a set of simulated scenarios where models run are repeated for perturbed physical parameters. In one or more embodiments, further computational cost savings can be achieved by optimizing a machine learning model of the congruency training procedure. At the bottom of the figure, as an example, congruency training can be repeated for several ventricular anatomies described by sets of geometric parameters, e.g., $\{R_b, L, Z, H, e, \Psi_0\}_i$ (on the left). In this example, these parameters can constitute the training set for a machine learning model, this model mapping geometric parameters to trained parameters (see bottom portion of figure). Based on this approach, transformation modules for arbitrary additional geometries can then be sized directly by the machine learning model. Repetitive description of like elements and/or processes employed in respective embodiments is omitted for sake of brevity.

Figure 22:
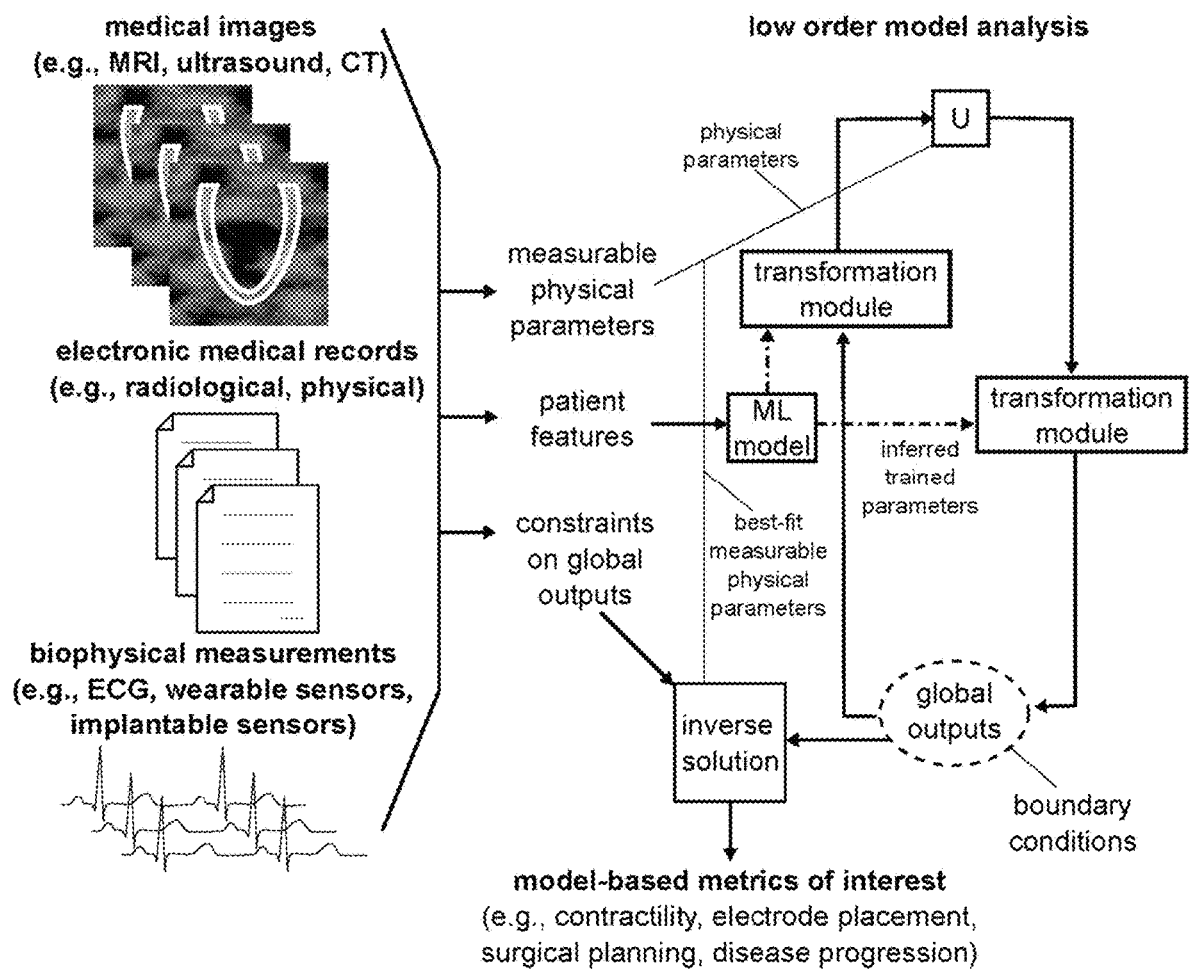

FIG. 22 depicts an embodiment where a low-order model can be connected to data sources gathered during clinical practice, such as medical imaging (e.g., MRI, CT, ultrasound), electronic medical reports (e.g., radiological reports, physical exam reports, medical lab tests), and biophysical measurements (e.g., from electrocardiogram, wearable sensors, implantable devices). Repetitive description of like elements and/or processes employed in respective embodiments is omitted for sake of brevity.

In this example, the data sources can provide valuable information to personalize the low-order model to the specifics of a clinical case. For example, certain physical parameters used by the model to modulate the behavior of the unit U can be, in some embodiments, directly measured in clinical assessments. Parameters for the transformation module could be instead inferred from patient-specific features via machine learning (see, e.g., the embodiment depicted in FIG. 21). Other physical parameters that can be required by the model might not be measured directly, and iterative solution of an inverse problem can therefore be necessary to ensure that model global outputs are limited by constraints indicated by the data sources. After personalization, in one or more embodiments, the low-order model can provide metrics of possible interest to assist clinical decisions, such as novel measures of contractility, optimized locations for electrode placement, indications for surgical planning, and predictions on disease progression scenarios.

In one or more embodiments a wearable device (e.g., smartwatch, fitness band, etc.) can measure physical signals from a subject, and this collected data can be used by one or more embodiments, e.g., for transformation of a model and/or as input into a model to yield results (e.g., by employing query component 151). In one or more embodiments, collected data can include values for fewer parameters than is required for a particular result or transformation. In this example, as noted above, the physical parameters that can be required by the model can be derived (e.g., by model generator 154 and/or query component 151) from different approaches based on existing data, e.g., using personalization described above, or by selecting values based on default values.

The present invention may be a system, a method, an apparatus and/or a computer program product at any possible technical detail level of integration. The computer program product can include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium can be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium can also include the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network can comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device. Computer readable program instructions for carrying out operations of the present invention can be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions can execute entirely on the user's computer, partly on the user's computer, as a stand-alone software package, partly on the user's computer and partly on a remote computer or entirely on the remote computer or server. In the latter scenario, the remote computer can be connected to the user's computer through any type of network, including a local area network (LAN) or a wide area network (WAN), or the connection can be made to an external computer (for example, through the Internet using an Internet Service Provider). In some embodiments, electronic circuitry including, for example, programmable logic circuitry, field-programmable gate arrays (FPGA), or programmable logic arrays (PLA) can execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions. These computer readable program instructions can be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions can also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks. The computer readable program instructions can also be loaded onto a computer, other programmable data processing apparatus, or other device to cause a series of operational acts to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which comprises one or more executable instructions for implementing the specified logical function(s). In some alternative implementations, the functions noted in the blocks can occur out of the order noted in the Figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While the subject matter has been described above in the general context of computer-executable instructions of a computer program product that runs on a computer and/or computers, those skilled in the art will recognize that this disclosure also can or can be implemented in combination with other program modules. Generally, program modules include routines, programs, components, data structures, etc. that perform particular tasks and/or implement particular abstract data types. Moreover, those skilled in the art will appreciate that the inventive computer-implemented methods can be practiced with other computer system configurations, including single-processor or multiprocessor computer systems, mini-computing devices, mainframe computers, as well as computers, hand-held computing devices (e.g., PDA, phone), microprocessor-based or programmable consumer or industrial electronics, and the like. The illustrated aspects can also be practiced in distributed computing environments in which tasks are performed by remote processing devices that are linked through a communications network. However, some, if not all aspects of this disclosure can be practiced on stand-alone computers. In a distributed computing environment, program modules can be located in both local and remote memory storage devices.

As used in this application, the terms "component," "system," "platform," "interface," and the like, can refer to and/or can include a computer-related entity or an entity related to an operational machine with one or more specific functionalities. The entities disclosed herein can be either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components can reside within a process and/or thread of execution and a component can be localized on one computer and/or distributed between two or more computers. In another example, respective components can execute from various computer readable media having various data structures stored thereon. The components can communicate via local and/or remote processes such as in accordance with a signal having one or more data packets (e.g., data from one component interacting with another component in a local system, distributed system, and/or across a network such as the Internet with other systems via the signal). As another example, a component can be an apparatus with specific functionality provided by mechanical parts operated by electric or electronic circuitry, which is operated by a software or firmware application executed by a processor. In such a case, the processor can be internal or external to the apparatus and can execute at least a part of the software or firmware application. As yet another example, a component can be an apparatus that provides specific functionality through electronic components without mechanical parts, wherein the electronic components can include a processor or other means to execute software or firmware that confers at least in part the functionality of the electronic components. In an aspect, a component can emulate an electronic component via a virtual machine, e.g., within a cloud computing system.

In addition, the term "or" is intended to mean an inclusive "or" rather than an exclusive "or." That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. Moreover, articles "a" and "an" as used in the subject specification and annexed drawings should generally be construed to mean "one or more" unless specified otherwise or clear from context to be directed to a singular form. As used herein, the terms "example" and/or "exemplary" are utilized to mean serving as an example, instance, or illustration. For the avoidance of doubt, the subject matter disclosed herein is not limited by such examples. In addition, any aspect or design described herein as an "example" and/or "exemplary" is not necessarily to be construed as preferred or advantageous over other aspects or designs, nor is it meant to preclude equivalent exemplary structures and techniques known to those of ordinary skill in the art.

As it is employed in the subject specification, the term "processor" can refer to substantially any computing processing unit or device comprising, but not limited to, single-core processors; single-processors with software multithread execution capability; multi-core processors; multi-core processors with software multithread execution capability; multi-core processors with hardware multithread technology; parallel platforms; and parallel platforms with distributed shared memory. Additionally, a processor can refer to an integrated circuit, an application specific integrated circuit (ASIC), a digital signal processor (DSP), a field programmable gate array (FPGA), a programmable logic controller (PLC), a complex programmable logic device (CPLD), a discrete gate or transistor logic, discrete hardware components, or any combination thereof designed to perform the functions described herein. Further, processors can exploit nano-scale architectures such as, but not limited to, molecular and quantum-dot based transistors, switches and gates, in order to optimize space usage or enhance performance of user equipment. A processor can also be implemented as a combination of computing processing units. In this disclosure, terms such as "store," "storage," "data store," data storage," "database," and substantially any other information storage component relevant to operation and functionality of a component are utilized to refer to "memory components," entities embodied in a "memory," or components comprising a memory. It is to be appreciated that memory and/or memory components described herein can be either volatile memory or nonvolatile memory, or can include both volatile and nonvolatile memory. By way of illustration, and not limitation, nonvolatile memory can include read only memory (ROM), programmable ROM (PROM), electrically programmable ROM (EPROM), electrically erasable ROM (EEPROM), flash memory, or nonvolatile random access memory (RAM) (e.g., ferroelectric RAM (FeRAM). Volatile memory can include RAM, which can act as external cache memory, for example. By way of illustration and not limitation, RAM is available in many forms such as synchronous RAM (SRAM), dynamic RAM (DRAM), synchronous DRAM (SDRAM), double data rate SDRAM (DDR SDRAM), enhanced SDRAM (ESDRAM), Synchlink DRAM (SLDRAM), direct Rambus RAM (DRRAM), direct Rambus dynamic RAM (DRDRAM), and Rambus dynamic RAM (RDRAM). Additionally, the disclosed memory components of systems or computer-implemented methods herein are intended to include, without being limited to including, these and any other suitable types of memory.

What has been described above include mere examples of systems and computer-implemented methods. It is, of course, not possible to describe every conceivable combination of components or computer-implemented methods for purposes of describing this disclosure, but one of ordinary skill in the art can recognize that many further combinations and permutations of this disclosure are possible. Furthermore, to the extent that the terms "includes," "has," "possesses," and the like are used in the detailed description, claims, appendices and drawings such terms are intended to be inclusive in a manner similar to the term "comprising" as "comprising" is interpreted when employed as a transitional word in a claim.

The descriptions of the various embodiments have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method, comprising:
identifying, by a system operatively coupled to a processor, a plurality of parameters of a multiscale model of a plurality of entities;
generating, by the system, a low-order model of an entity based on collected data of an operation of the entity, wherein the low-order model of the entity comprises a plurality of transformation modules and a subset of the plurality of parameters; and
training, by the system, the low-order model of the entity based on information from the multiscale model of the plurality of entities corresponding to the subset of the plurality of parameters, wherein the transforming the model of the entity results in a first result from the multiscale model of the plurality of entities and a second result from the low-order model of the entity having a relationship that satisfies a defined criterion, given same values used for the subset of the plurality of parameters, wherein the training comprises generating trained parameters for the transformation modules that modulate transformation of outputs of the low-order model to match outputs of the multiscale model according to the defined criterion, wherein the training further comprises an active training simulation to determine active coefficients and a passive training simulation to determine passive coefficients, and wherein the active coefficients and the passive coefficients maximize congruence between the outputs of the low-order model and the outputs of the multiscale model.

2. The computer-implemented method of claim 1, further comprising:
segmenting, by the system, an image of the entity into a plurality of segments of the entity based on analysis of the image, wherein ones of the plurality of segments comprise physical characteristics of the plurality of segments; and
determining, by the system, a result of the low-order model of the entity based on the physical characteristics being used as values for the subset of the plurality of parameters.

3. The computer-implemented method of claim 2, wherein the image of the entity is a medical image, and wherein the entity is a part of a biological system of a biological entity.

4. The computer-implemented method of claim 1, wherein the defined criterion corresponds to a level of similarity between the first result and the second result.

5. The computer-implemented method of claim 1, wherein the subset of the plurality of parameters correspond to physical characteristics of the entity and are monitored by a wearable device, and wherein the method further comprises:
selecting, by the system, values for the subset of the plurality of parameters not corresponding to the monitored physical characteristics; and
determining, by the system, a result of the low-order model of the entity based on the subset of the plurality of parameters, and the monitored portion of the subset, being used as values for the subset of the plurality of parameters.

6. The computer-implemented method of claim 5, wherein the monitored physical characteristics of the entity are physical characteristics of cardiac performance, and wherein the selected values are selected based on characteristics of the entity.

7. The computer-implemented method of claim 1, wherein the multiscale model of the plurality of entities is a finite element model.

8. The computer-implemented method of claim 1, wherein the transforming the model of the entity comprises:
mapping, by the system, ones of the plurality of parameters of the multiscale model of the plurality of entities to the subset of the plurality of parameters; and
employing, by the system, congruency training to modify the low-order model of the entity based on the mapped ones of the plurality of parameters.

9. The computer-implemented method of claim 1, further comprising transforming, by the system, the multiscale model of the plurality of entities based on the trained low-order model of the entity.

10. A system, comprising:
a memory that stores computer executable components; and
a processor that executes the computer executable components stored in the memory, wherein the computer executable components comprise:
a parameter identifying component that identifies a plurality of parameters of a multiscale model of a plurality of entities;
a model generator that generates a low-order model of an entity based on collected data of an operation of the entity, wherein the low-order model of the entity comprises a plurality of transformation modules and a subset of the plurality of parameters; and
a model transformer that trains the low-order model of the entity based on information from the multiscale model of the plurality of entities corresponding to the subset of the plurality of parameters, wherein the transforming the model of the entity results in a first result from the multiscale model of the plurality of entities and a second result from the low-order model of the entity having a relationship that satisfies a defined criterion, given same values used for the subset of the plurality of parameters, wherein the training comprises generating trained parameters for the transformation modules that modulate transformation of outputs of the low-order model to match outputs of the multiscale model according to the defined criterion, wherein the training further comprises an active training simulation to determine active coefficients and a passive training simulation to determine passive coefficients, and wherein the active coefficients and the passive coefficients maximize congruence between the outputs of the low-order model and the outputs of the multiscale model.

11. The system of claim 10, wherein the computer executable components further comprise a query component that determines a result of the low-order model of the entity based on physical characteristics of ones of a plurality of segments being used as values for the subset of the plurality of parameters, and wherein the ones of the plurality of segments are based on analysis of an image.

12. The system of claim 11, wherein the image of the entity is a medical image, and wherein the entity is a part of a biological system of a biological entity.

13. The system of claim 10, wherein the defined criterion corresponds to a level of similarity between the first result and the second result.

14. The system of claim 10, wherein a portion of the subset of the plurality of parameters correspond to physical characteristics of the entity and are monitored by a wearable device, and wherein the computer executable components further comprise a query component that:
    selects values for the subset of the plurality of parameters not corresponding to the monitored physical characteristics; and
    determines a result of the low-order model of the entity based on the subset of the selected values, and the monitored portion of the subset, being used as values for the subset of the plurality of parameters.

15. The system of claim 14, wherein the monitored physical characteristics of the entity are physical characteristics of cardiac performance, and wherein the selected values are selected based on characteristics of the entity.

16. The system of claim 10, wherein the multiscale model of the plurality of entities is a finite element model.

17. The system of claim 10, wherein the model transformer further:
    maps ones of the plurality of parameters of the multiscale model of the plurality of entities to the subset of the plurality of parameters; and
    employs congruency training to modify the low-order model of the entity based on the mapped ones of the plurality of parameters.

18. The system of claim 10, wherein the model transformer further transforms the multiscale model of the plurality of entities based on the trained low-order model of the entity.

19. A computer program product facilitating training of a low-order model of an entity by a multiscale model of a plurality of entities, the computer program product comprising a computer readable storage medium having program instructions embodied therewith, the program instructions executable by a processor to cause the processor to:
    identify, by the processor, a plurality of parameters of the multiscale model of a plurality of entities;
    generate, by the processor, the low-order model of an entity based on collected data of an operation of the entity, wherein the low-order model of the entity comprises a plurality of transformation modules and a subset of the plurality of parameters; and
    train, by the processor, the low-order model of the entity based on information from the multiscale model of the plurality of entities corresponding to the subset of the plurality of parameters, wherein the transforming the model of the entity results in a first result from the multiscale model of the plurality of entities and a second result from the low-order model of the entity having a relationship that satisfies a defined criterion, given same values used for the subset of the plurality of parameters, wherein the training comprises generating trained parameters for the transformation modules that modulate transformation of outputs of the low-order model to match outputs of the multiscale model according to the defined criterion, wherein the training further comprises an active training simulation to determine active coefficients and a passive training simulation to determine passive coefficients, and wherein the active coefficients and the passive coefficients maximize congruence between the outputs of the low-order model and the outputs of the multiscale model.

20. The computer program product of claim 19, wherein the program instructions are further executable by the processor to cause the processor to:
    segment, by the processor, an image of the entity into a plurality of segments of the entity based on analysis of the image, wherein ones of the plurality of segments comprise physical characteristics of the segment; and
    determine, by the processor, a result of the low-order model of the entity based on the physical characteristics being used as values for the subset of the plurality of parameters.

* * * * *